(12) United States Patent
Charles et al.

(10) Patent No.: US 6,665,554 B1
(45) Date of Patent: Dec. 16, 2003

(54) MEDICAL MANIPULATOR FOR USE WITH AN IMAGING DEVICE

(76) Inventors: Steve T. Charles, 3220 Oak Manor, Germantown, TN (US) 38138; J. Michael Stuart, 46 Judy Ct., Corrales, NM (US) 87048

( * ) Notice: Subject to any disclaimer, the term of this patent is extended or adjusted under 35 U.S.C. 154(b) by 0 days.

(21) Appl. No.: 09/442,966

(22) Filed: Nov. 18, 1999

Related U.S. Application Data
(60) Provisional application No. 60/109,074, filed on Nov. 18, 1998.

(51) Int. Cl.[7] ................................................. A61B 5/00

(52) U.S. Cl. ...................... 600/427; 600/429; 606/130
(58) Field of Search .................... 600/427, 429; 606/130; 378/68, 177, 208, 209

(56) References Cited

U.S. PATENT DOCUMENTS

| | | |
|---|---|---|
| 3,923,166 A | 12/1975 | Fletcher et al. |
| 3,949,747 A | 4/1976 | Hevesy |
| 4,401,433 A | 8/1983 | Luther |
| 4,573,452 A | 3/1986 | Greenberg |
| 4,653,509 A | 3/1987 | Oloff et al. |
| 5,053,687 A | 10/1991 | Merlet |
| 5,078,140 A | 1/1992 | Kwoh |
| 5,081,381 A | 1/1992 | Narasaki |
| 5,086,401 A | 2/1992 | Glassman et al. |
| 5,142,930 A | 9/1992 | Allen et al. |
| 5,161,542 A | 11/1992 | Palestrant |
| 5,186,174 A | 2/1993 | Schlondorff et al. |
| 5,219,351 A * | 6/1993 | Teubner et al. ............. 606/130 |
| 5,234,000 A | 8/1993 | Hakky et al. |
| 5,240,011 A | 8/1993 | Assa |
| 5,251,127 A | 10/1993 | Raab |
| 5,279,309 A | 1/1994 | Taylor et al. |
| 5,280,427 A | 1/1994 | Magnusson et al. |
| 5,299,288 A | 3/1994 | Glassman et al. |
| 5,305,203 A | 4/1994 | Raab |
| 5,343,385 A | 8/1994 | Joskowicz et al. |
| 5,354,158 A | 10/1994 | Sheldon et al. |
| 5,383,454 A | 1/1995 | Bucholz |
| 5,389,101 A | 2/1995 | Heilbrun et al. |
| 5,397,323 A | 3/1995 | Taylor et al. |
| 5,402,801 A | 4/1995 | Taylor |
| 5,408,409 A | 4/1995 | Glassman et al. |
| 5,409,497 A | 4/1995 | Siczek et al. |
| 5,415,182 A | 5/1995 | Chin et al. |
| 5,417,210 A | 5/1995 | Funda et al. |
| 5,425,616 A | 6/1995 | Arai et al. |
| 5,445,166 A | 8/1995 | Taylor |
| 5,464,013 A | 11/1995 | Lemelson |
| 5,494,034 A | 2/1996 | Schlondorff et al. |
| 5,564,436 A | 10/1996 | Hakky et al. |
| 5,568,593 A | 10/1996 | Demarest et al. |
| 5,572,999 A | 11/1996 | Funda et al. |
| 5,575,798 A * | 11/1996 | Koutrouvelis ............... 606/130 |
| 5,584,292 A | 12/1996 | Cheung |
| 5,628,327 A | 5/1997 | Unger et al. |
| 5,630,431 A | 5/1997 | Taylor |
| 5,643,286 A | 7/1997 | Warner et al. |
| 5,647,373 A | 7/1997 | Paltieli |
| 5,695,500 A | 12/1997 | Taylor et al. |
| 5,748,767 A | 5/1998 | Raab |
| 5,749,362 A | 5/1998 | Funda et al. |
| 5,769,086 A * | 6/1998 | Ritchart et al. ............. 600/566 |
| 5,776,153 A | 7/1998 | Rees |
| 5,782,764 A | 7/1998 | Werne |
| 5,800,423 A | 9/1998 | Jensen |
| 5,803,912 A | 9/1998 | Siczek et al. |

(List continued on next page.)

*Primary Examiner*—Ruth S. Smith
(74) *Attorney, Agent, or Firm*—Leydig, Voit & Mayer, Ltd.

(57) ABSTRACT

A manipulator for use in medical procedures can manipulate a medical tool with one or more degrees of freedom with respect to a patient. The manipulator is particularly useful for positioning a medical tool with respect to a patient disposed inside an imaging device such as a computer tomography machine.

25 Claims, 21 Drawing Sheets

U.S. PATENT DOCUMENTS

| | | |
|---|---|---|
| 5,806,518 A | 9/1998 | Mittelstadt |
| 5,820,623 A * | 10/1998 | Ng .................................. 606/1 |
| 5,833,656 A | 11/1998 | Smith et al. |
| 5,851,183 A | 12/1998 | Bucholz |
| 5,865,744 A | 2/1999 | Lemelson |
| 5,887,121 A | 3/1999 | Funda et al. |
| 5,943,914 A | 8/1999 | Morimoto et al. |
| 5,950,629 A | 9/1999 | Taylor et al. |
| 5,951,475 A | 9/1999 | Gueziec et al. |
| 5,976,156 A | 11/1999 | Taylor et al. |
| 6,000,297 A | 12/1999 | Morimoto et al. |
| 6,021,342 A | 2/2000 | Brabrand |
| 6,024,695 A | 2/2000 | Taylor et al. |
| 6,110,112 A * | 8/2000 | Heywang-Koebrunner . 600/439 |
| 6,149,592 A * | 11/2000 | Yanof et al. ................. 600/427 |
| 6,245,028 B1 * | 6/2001 | Furst et al. ................. 600/568 |

* cited by examiner

MEDICAL MANIPULATOR FOR USE WITH AN IMAGING DEVICE

REFERENCE TO RELATED APPLICATIONS

This application claims the benefit of U.S. Provisional Application No. 60/109,074 filed on Nov. 18, 1998, which is incorporated by reference.

BACKGROUND OF THE INVENTION

1. Field of the Invention

This invention relates to a manipulator, and particularly to a manipulator suitable for use in conjunction with medical imaging devices.

2. Description of the Related Art

Medical biopsies and other medical procedures are frequently performed in conjunction with imaging equipment, such as CT (computer tomography) equipment, conventional x-ray equipment, magnetic resonance imaging equipment, or other imaging equipment. In a biopsy performed with such imaging equipment, a biopsy needle is inserted into a patient's body while the patient is outside the imaging equipment, the patient is placed inside the imaging equipment, and then an image is taken of the patient's body with the imaging equipment to determine the location of the biopsy needle with respect to the region where the biopsy is to be performed. It is frequently difficult or unsafe for a human operator to adjust the position of the biopsy needle while an image of the patient's body is being taken due to the small amount of space between the interior of the imaging equipment and the patient's body, due to the undesirability of the operator being exposed to radiation from the imaging equipment, or due to the operator interfering with imaging if standing close enough to the patient to manipulate the biopsy needle. Therefore, each time the position of the biopsy needle needs to be adjusted, the patient must be withdrawn from the imaging equipment, and after the position of the biopsy needle has been changed, the patient is reintroduced into the imaging equipment and the location of the biopsy needle is again checked. Since the operator cannot view the position of the biopsy needle within the patient's body as he adjusts the position, the process of positioning the biopsy needle is essentially one of trial and error and so can be time-consuming and imprecise. The same problems occur with procedures other than biopsies, such as during the insertion of catheters.

SUMMARY OF THE INVENTION

The present invention provides a manipulator capable of inserting a needle or other object into a patient's body for diagnostic or therapeutic purposes and adjusting the position of the needle within the patient's body while imaging of the patient's body and the needle or other object is being carried out.

The present invention also provides an input device for use in controlling such a manipulator.

The present invention further provides an apparatus for inserting an object into a patient's body.

The present invention additionally provides a biopsy needle which can be assembled from a plurality of needle sections. The present invention still further provides methods for performing medical procedures.

According to one form of the present invention, a manipulator is capable of manipulating a medical tool with respect to a patient with at least one degree of freedom and preferably with multiple degrees of freedom.

In preferred embodiments, the tool can be manipulated with five degrees of freedom.

In preferred embodiments, the manipulator may be sufficiently small to readily fit into the space within an imaging device between a patient's body and an interior wall of the imaging device, but the manipulator can also be used to manipulate a medical tool with respect to a patient who has been removed from an imaging device.

A manipulator according to the present invention can be used with any type of imaging equipment, including computer tomography machines, magnetic resonance imaging machines, conventional x-ray machines, fluoroscopy systems, and ultrasonic imaging systems. However, it can also be used in applications not involving imaging. The image may be displayed for the operator in any convenient manner, such as on a CRT or other type of electronic display, or in the form of a printed image on a sheet.

In one mode of operation, the manipulator introduces a medical tool into a field of view of the imaging device while imaging is taking place, so that an operator can view an actual image of the tool. In another mode of operation, the manipulator introduces a medical tool into a region of the patient's body after imaging of the region has taken place, and a virtual image of the medical tool is superimposed on an actual image of the region to indicate to the operator the location of the medical tool with respect to the region.

A manipulator according to the present invention can be used to manipulate a wide variety of medical tools both for therapeutic and diagnostic purposes, a few examples of which are biopsy needles, biopsy guns, various probes including cryo probes and radio frequency probes, lasers, laser hyperthermia devices, cameras, and needles for administering various substances, such as biotherapeutic agents, alcohol, or radioactive pellets, to the interior of a patient's body. In addition to tools which are inserted into a patient's body, it can be used to manipulate tools which are normally utilized on a patient's skin.

A manipulator according to the present invention may be operated in a master-slave mode, a fully robotic mode, or a semi-robotic mode in which some of the motions of the manipulator are controlled by input commands from an operator and other motions are controlled automatically.

The manipulator can be controlled by various input devices. According to one form of the invention in which the manipulator operates in a mater-slave mode, the manipulator can be controlled by a haptic input device which provides force feedback to the hand of the operator of the input device. The force feedback may be indicative of the resistance to movement encountered by the medical tool. The force feedback may also be controlled so as to assist the operator in more safely guiding the medical tool. For example, the force feedback can be controlled so as to inhibit the operator from moving the tool to the vicinity of delicate objects within the patient's body.

A manipulator according to the present invention is particularly suitable for manipulating needles, such as biopsy needles. According to one form of the present invention, a needle for use with a manipulator can be assembled from a plurality of needle sections. The needle may be assembled while imaging of a patient is taking place immediately before the needle is inserted into the patient, and the needle may be disassembled into the individual needle sections as it is being withdrawn from the patient. The ability to assembly a needle from a plurality of needle sections makes the insertion of an elongated needle into a patient much easier and enables the manipulator to be introduced into crowded spaces which could not be accessed with a one-piece needle of the same length.

A manipulator according to the present invention enables a medical tool to be manipulated inside tight spaces in which it would be difficult or impossible for a human operator to position a tool or in environments which would be unsafe for a human operator. In particular, the manipulator can manipulate a medical tool with respect to a patient inside imaging equipment, which tend to have very small clearance surrounding a patient's body during imaging. Therefore, the manipulator enables the position of a medical tool with respect to a patient to be adjusted while imaging is taking place and makes it unnecessary to remove the patient from the imaging equipment each time the position of the tool needs to be adjusted. For this reason, the medical tool can be positioned quickly and accurately, enabling a medical procedure to be performed with the tool efficiently and economically with less stress on the patient. The ability of the tool to be rapidly positioned is particularly advantageous when the tool is being positioned in or near the patient's chest and the patient is holding his breath.

The manipulator can also reduce the fatigue experienced by a human operator, since it is unnecessary for the operator to physically support the medical tool during manipulation. The operator can let go of the manipulator while performing other tasks without the medical tool undergoing movement. Thus, the positional stability of the medical tool can be improved compared to when it is supported by hand. The ability of the operator to perform other tasks while the medical tool is supported by the manipulator can increase work efficiency and enable him to complete imaging more rapidly.

Furthermore, the manipulator can enhance the dexterity of the operator, i.e., it can enable him to manipulate a medical tool with greater dexterity than he could if directly handling the tool in his hands. For example, the manipulator can scale up or down the magnitudes of the operator's hand motions or the forces he applies, it can eliminate the effects of tremor in his hands, and it can help him to guide the tool along a path avoiding delicate regions of the patient's body.

DESCRIPTION OF PREFERRED EMBODIMENTS

Figure 1:
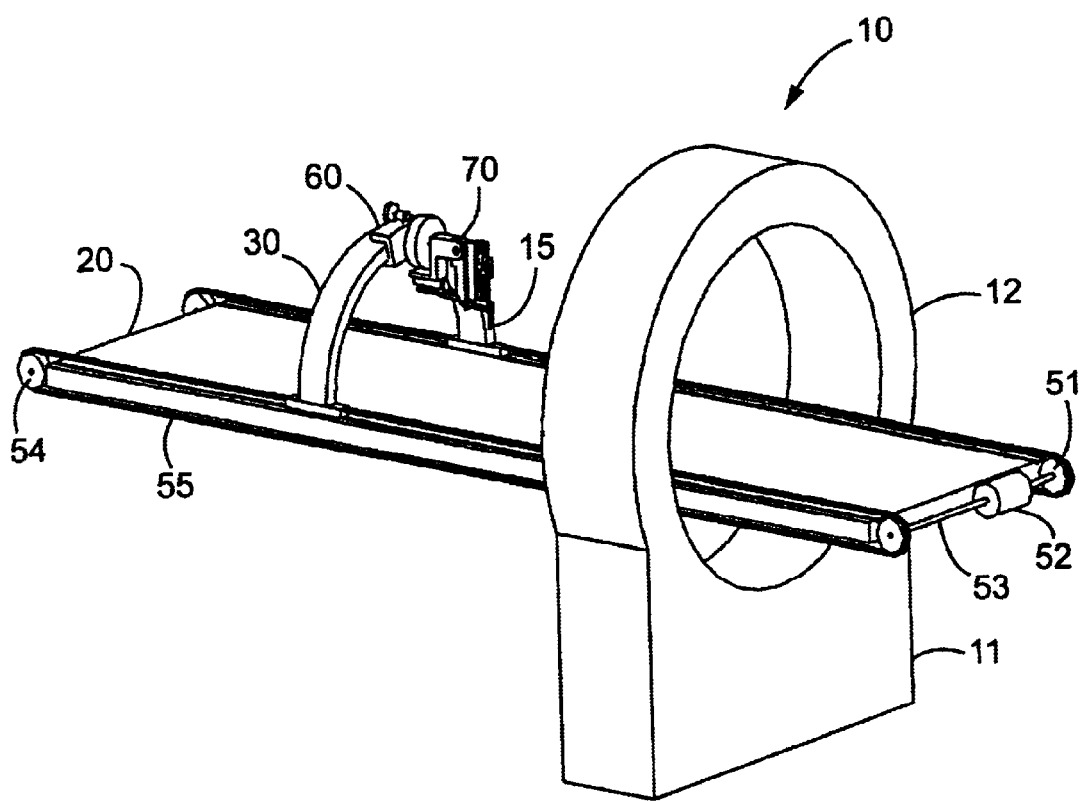
FIG. 1 is a schematic isometric view of an embodiment of a manipulator according to the present invention installed on a computer tomography machine.
Figure 2:
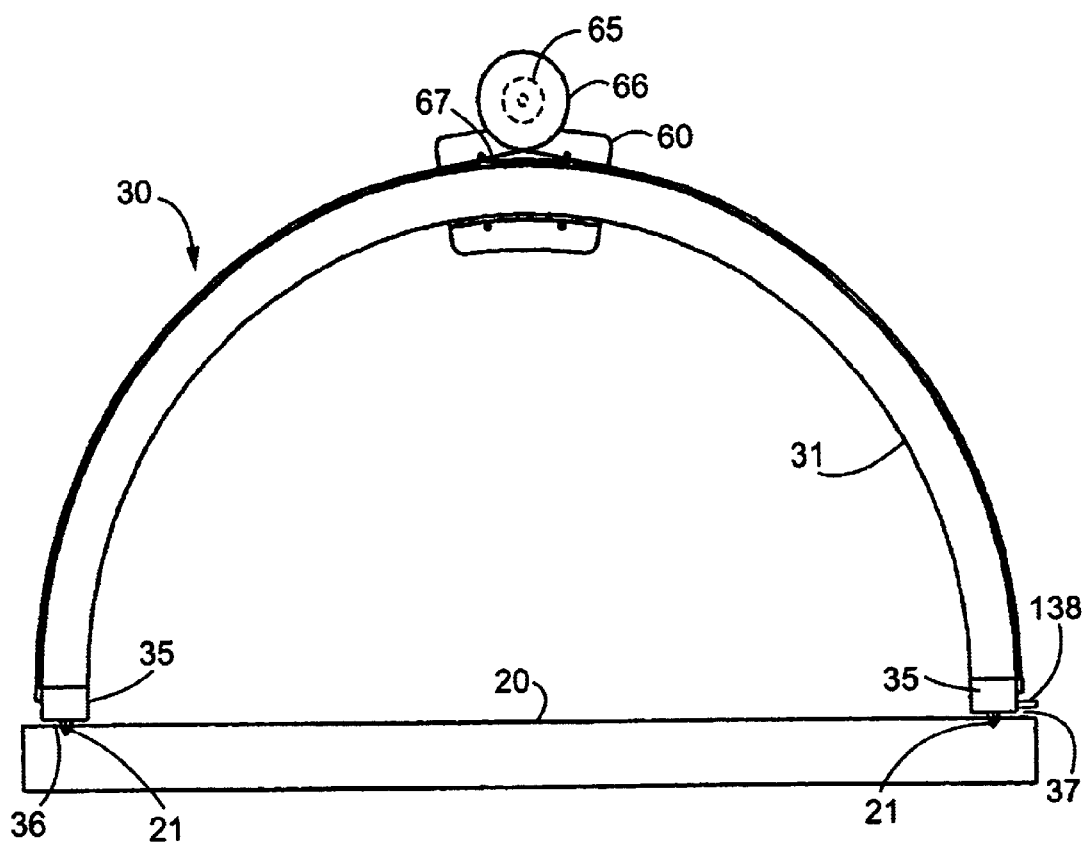
FIG. 2 is a schematic front elevation of the guide of the embodiment of FIG. 1.

FIG. 1 schematically illustrates an embodiment of a manipulator according to the present invention for manipulating a medical tool. The manipulator is shown installed on a computer tomography (CT) machine 10, but as explained above, a manipulator according to the present invention can be used with other types of imaging devices and can also be employed separately from an imaging device.

The computer tomography machine 10, which may be of any desired type, typically includes a base 11, a donut-shaped portion, usually referred to as a gantry 12, mounted on the base 11 and containing imaging equipment, and a table 20 for supporting a patient during imaging. The table 20, which may be supported by the base 11 or other structure, is usually movable in its lengthwise direction through the gantry 12 to position the patient with respect to the imaging equipment within the gantry 12.

The manipulator includes a guide 30, a carriage 60 mounted on the guide 30 for movement above a patient lying on the table 20, and a positioning mechanism 70 mounted on the carriage 60 for positioning a biopsy needle 15 or other medical tool with respect to a patient lying on the table 20. In the following description, the operation and structure of the manipulator will be explained with respect to when the manipulator is positioning a biopsy needle, but in general the same explanation will apply when the manipulator is positioning a different medical tool. The guide 30 is preferably movable with respect to the table 20 in the lengthwise direction of the table 20 to enable the biopsy needle 15 to be moved to any desired location along the length of a patient. The guide 30 can preferably also move with the table 20 so as to be capable of maintaining a constant position with respect to a patient on the table 20 when the table 20 is moving so that the position of the needle 15 relative to the patient will not change. However, it is possible for the guide 30 to be fixed with respect to the gantry 12 of the CT machine 10 so that positioning of the needle 15 in the lengthwise direction of a patient is accomplished by movement of the table 20 rather than by movement of the guide 30.

The guide 30 can have any shape which enables it to pass above a patient lying on the table 20 and to introduce the needle 15 into the imaging field of the CT machine 10. In preferred embodiments, the guide 30 comprises an arch 31 having a shape similar to the shape of the bore of the gantry 12 of the CT machine 10. For example, when the bore in the gantry 12 is circular, the arch 31 may have the shape of an arc of a circle. However, the arch 31 may have other shapes, such as polygonal, oval, straight, or a combination of curved and straight shapes. The arch 31 of the illustrated guide 30 has an outer diameter smaller than the inner diameter of the bore of the gantry 12 so that the guide 30 can pass through the bore, but as long as the biopsy needle 15 or other medical tool can be positioned in the imaging field of the imaging device, the dimensions of the guide 30 are not critical.

The guide 30 may be supported for movement by any suitable structure, such as by the table 20, the gantry 12, another portion of the CT machine 10, the floor on which the CT machine 10 is mounted, the ceiling, or a wall of a room in which the CT machine 10 is disposed. In the present embodiment, the guide 30 is supported by the table 20. The guide 30 may be supported on both widthwise sides of the table 20, or it may be supported on only one side, with the opposite widthwise end of the guide 30 being unsupported like a cantilever beam.

In the illustrated embodiment, the guide 30 extends perpendicular to the lengthwise direction of the table 20, but there is no restriction on the orientation of the guide 30.

Figure 3:
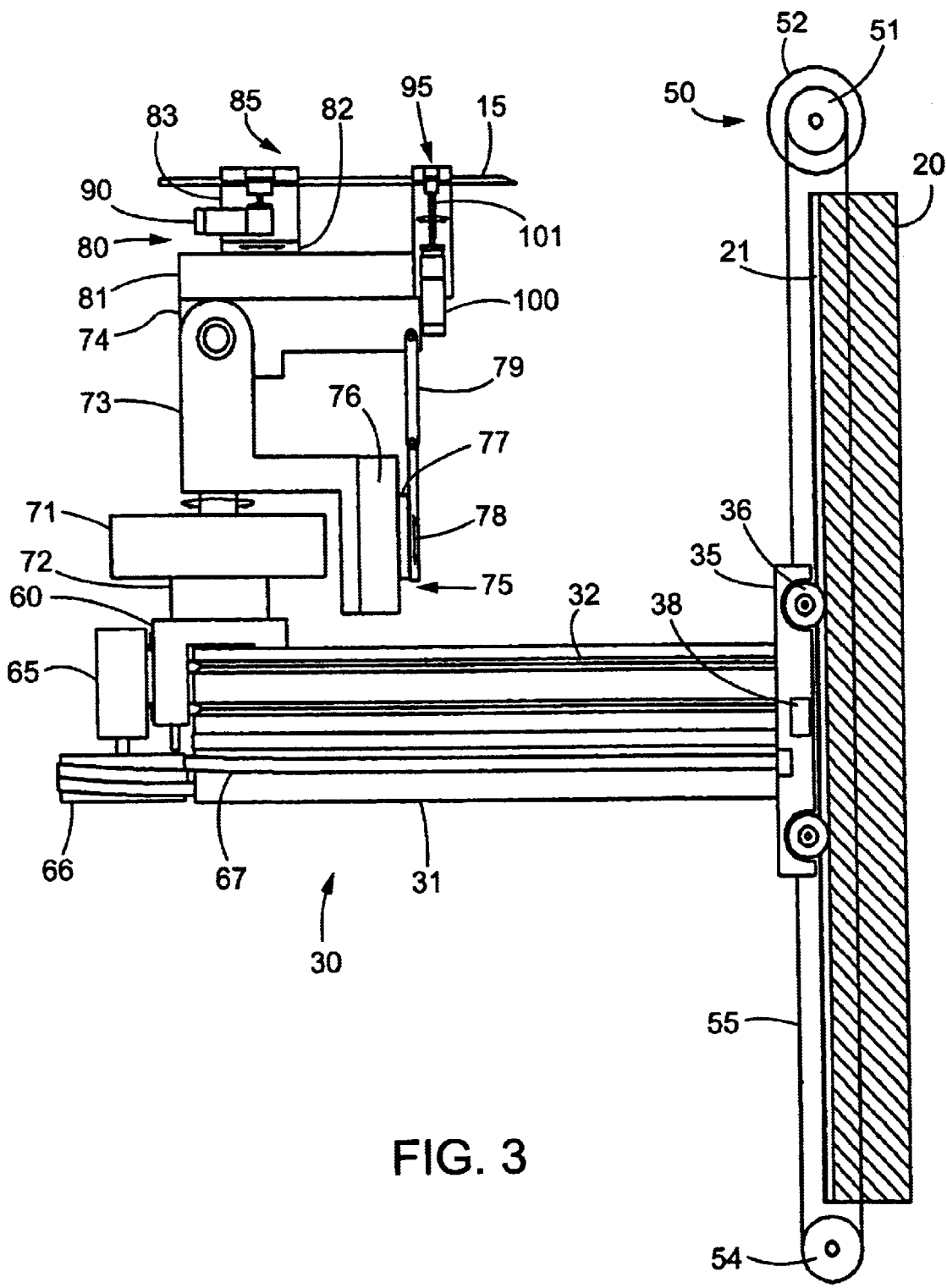
FIG. 3 is a schematic side elevation of the embodiment of FIG. 1.

The guide 30 may be manually movable in the lengthwise direction of the table 20, or a drive mechanism may be provided, either as part of or separate from the guide 30, for translating the guide 30 in the lengthwise direction of the table 20. FIG. 3 is a partially cross-sectional side elevation illustrating one example of a drive mechanism 50 for the guide 30. The guide 30 includes two bases 35, each of which supports one of the ends of the arch 31. The bases 35 are supported by the table 20 so as to be able to smoothly move in the lengthwise direction of the table 20. For example, in the present embodiment, each base 35 is equipped with a plurality of wheels 36 which are guided by grooves 21 formed in the upper surface of the table 20 and extending in the lengthwise direction of the table 20 so that the guide 30 can roll along the table 20. A drive pulley 51 and a driven pulley 54 are disposed at opposite lengthwise ends of the table 20, and a belt 55 having its opposite ends secured to one of the bases 35 passes around both of the pulleys 51, 54. The drive pulley 51 can be rotated by a rotary electric motor 52 or other type of actuator capable of producing rotation, and the engagement between the drive pulley 51 and the belt 55 causes the belt 55 to pull the guide 30 to the right or left in FIG. 3 in the lengthwise direction of the table 20. The motor 52 may be equipped with a gear train if torque amplification is desired. A harmonic gear train is particularly suitable because it produces zero backlash and can provide smooth, precise control of the movement of the guide 30, but any other type of gear train may instead be used. A drive force for translating the guide 30 may be applied to one or both of the widthwise sides of the guide 30. For example, as shown in FIG. 1, pulleys 51, 54 and a belt 55 may be provided on both widthwise sides of the table 20, with each belt 55 connected to one of the bases 35 of the guide 30. The two belts 55 may be driven by separate motors, or a single motor 52 may be connected to the drive pulley 51 on each widthwise side of the table 20 by a shaft 53, for example. A drive force applied to both sides of the guide 30 may produce smoother movement, and the use of a single actuator, as in FIG. 1, for rotating the drive pulleys 51 ensures synchronous movement of both bases 35 of the guide 30. Many drive mechanisms other than that shown in FIG. 3 can be used for translating the guide 30, such as pneumatic or hydraulic cylinders, a lead screw arrangement, a rotary motor mounted on one or both of the bases 35 and rotating gears or rollers engaging the table 20 or rotating a capstan having a belt wound around it, or each base 35 can be mounted on a linear motor having a linear track extending in the lengthwise direction of the table 20.

If desired, the guide 30 may be equipped with a position sensor for determining the position of the guide 30 in the lengthwise direction of the table 20. For example, in this embodiment, an elongated scale 37 is mounted on the table 20, and a read head 38 is mounted on one of the bases 35 or other portion of the guide 30 in a position in which is it coupled to the scale 37 and can sense the position of the guide 30 with respect to the scale 37. One example of a position sensor which is particularly suitable is a an optical encoder such as that available from Renishaw PLC of Gloucestershire, UK, but many other types of position sensors can also be used. Other arrangements can also be used for determining the position of the guide 30, such as an encoder mounted on the motor of the drive mechanism 50, or a read head mounted on the table 20 which reads a scale attached to one of the belts 55.

The carriage 60 can be mounted on the guide 30 in any manner which enables it to move along the guide 30 to various locations with respect to a patient lying on the table 20. The carriage 60 may be slidably supported on the guide 30, or it may be supported by balls, wheels, rollers, air bearings, or other low friction mechanisms which permit the carriage 60 to translate along the guide 30. In the present embodiment, the carriage 60 is a generally U-shaped member having two opposing legs which oppose the radially inner and radially outer sides of the arch 31. Each leg is equipped with a plurality of wheels 61, each of which is received in a groove 32 extending in the circumferential direction of the arch 31 so that the carriage 60 can roll along the guide 30. Preferably, a drive mechanism is provided, typically on the guide 30 and/or the carriage 60, for moving the carriage 60 in the circumferential direction of the arch 31 while being guided by the grooves 32. In the illustrated embodiment, a drive mechanism for the carriage comprises an actuator in the form of a rotary motor 65 mounted on the carriage 60 and a capstan 66 secured to an output shaft of the motor 65. The motor 65 may be equipped with a gear train for torque amplification, with a harmonic gear train being particularly suitable because it does not produce backlash. A flexible member 67, such as a belt or a cable, rests on the arch 31 with its opposite ends immobilized with respect to the arch 31. The flexible member 67 passes around the capstan 66 one or more times so as to be in rolling contact with the capstan 66, preferably without slipping. When the capstan 66 is rotated by the motor 65, the frictional engagement between the flexible member 67 and the capstan 66 causes the carriage 60 to be pulled along the arch 31. For clarity, the separation between the capstan 66 and the radially outer surface of the arch 31 is exaggerated in the drawings. Preferably, the minimum separation is approximately equal to the thickness of the flexible member 67 so that the flexible member 67 is not pulled up from the surface of the arch 31 by the capstan 66 until the flexible member 67 is located directly beneath the capstan 66. A tension adjusting mechanism, such as an adjustment screw connected between the flexible member 67 and some portion of the guide 30, may be provided at one or both ends of the flexible member 67 to maintain it under a desired degree of tension. The illustrated drive mechanism employing a capstan 66 and a flexible member 67 has a simple structure, produces no backlash, and is capable of moving the carriage 60 in extremely small increments along the arch 31, but many other drive mechanisms can instead be used to translate the carriage 60. For example, the flexible member 67 may be omitted, and the capstan 66 may be replaced by a roller in rolling contact with the outer surface of the arch 31 or by a pinion which engages with a ring gear attached to the outer surface of the arch 31. A belt and pulley arrangement like that used to translate the guide 30 along the table 20 can also be used, or the carriage 60 can be secured to the moving portion of a linear motor having a curved track mounted on the arch 31 and extending in the circumferential direction of the arch 31.

If desired, a position sensor may be provided for sensing the position of the carriage 60 in the circumferential direction of the arch 31. In the illustrated embodiment, a flexible scale 68 is secured to the radially outer surface of the arch 31, and a read head 69, which is sensitive to the scale 68, is mounted on the carriage 60 opposing the scale 68. The scale 68 and the read head 69 may be similar to those used to sense the position of the guide 30 along the table 20. However, many other types of position sensing arrangement devices can also be employed, such as a rotary encoder mounted on the motor 65 for rotating the capstan 66.

The positioning mechanism 70 is capable of moving the needle 15 with respect to the guide 30 with one or more degrees of freedom so as to produce a desired orientation of the tool with respect to a patient lying on the table. The number of degrees of freedom with which the positioning mechanism 70 is capable of moving the tool can be selected based on the characteristics of the tool. When the tool is a member which is to be inserted into a patient's body, such as a needle 15, the positioning mechanism 70 is preferably capable of translating the tool in its lengthwise direction to insert or retract the tool with respect to the patient's body. It may also be convenient if the tool can be pivoted about a yaw axis and/or a pitch axis perpendicular to the lengthwise direction of the tool to make it possible to insert the tool into a patient's body from any desired angle. When the tool is a symmetrical object, such as a needle 15, it is generally unnecessary for the tool to be able to roll about its lengthwise axis, but it is also possible for the positioning mechanism 70 to produce a rolling motion of the tool. A rolling motion is useful when the tool is a camera or other device which may need to face in a particular direction about its lengthwise axis with respect to the interior of a patient's body. In the present embodiment, the positioning mechanism 70 includes an actuator in the form of a rotary motor 71 for producing a yawing motion mounted on the carriage 60 and having an output shaft 71a extending perpendicular to the plane of the arch 31, i.e., in the lengthwise direction of the table 20. A first frame 73 is secured to the output shaft 71a for rotation with the output shaft 71a, and a second frame 74 is pivotably supported by the first frame 73 for rotation about an axis perpendicular to the rotational axis of the output shaft 71a. A linear actuator 75 for rotating the second frame 74 to produce a pitching motion is mounted on the bottom of the first frame 73. The illustrated linear actuator 75 is a linear motor having a stationary magnet track 76 secured to the first frame 73 and a coil unit 77 movably mounted on the magnet track 76. A first link 78 is secured to the coil unit 77 for translation with the coil unit 77, and a second link 79 has one end pivotably connected to the first link 78 and a second end pivotably connected to the second frame 74. In this embodiment, the actuator 71 for producing pitching motion is supported by the actuator 71 for producing yawing motion, but an actuator for producing yawing motion may instead support an actuator for producing motion. The second frame 74 supports an insertion mechanism for translating the needle 15 in its lengthwise direction into or out of a patient's body. The insertion mechanism includes an upper clamp 85 capable of releasably grasping the needle 15, a guide in the form of a lower clamp 95 for guiding the needle 15 in the lengthwise direction, and an insertion axis actuator 80 for moving the upper clamp 85 in the lengthwise direction of the needle 15 to translate the needle 15 while the lower clamp 95 remains stationary with respect to the second frame 74. The provision of a guide for the needle 15 enables the angle of the needle 15 to be better controlled as it is being inserted into a patient, and the guide can also prevent the needle from bending or buckling under axial forces applied to it during insertion. A guide in the form of a clamp can vary the force with which it contacts the needle 15, but the guide may have any other structure which enables it to guide the needle. For example, it may comprise rollers between which the needle 15 can pass, or it can be a member with no moving parts, such as a plate with a hole through which the needle can pass. The insertion axis actuator 80 may be any type of device capable of translating one or both of the clamps 85,95. The illustrated actuator 80 comprises a linear motor having an elongated magnet track 81 and a coil unit 82 movable along the magnet track 81, but a pneumatic or hydraulic cylinder, a solenoid, or a rotary motor connected to a lead screw or other mechanism for converting rotary to linear motion can instead be employed. When the actuator 80 is a linear motor, to prevent the upper clamp 85 from falling downwards when power to the motor is cut off (either deliberately or accidentally), the linear motor may be equipped with a spring-loaded brake mechanism which is kept in a released state when power is applied to the motor but which is actuated to maintain the coil unit 82 stationary when power to the motor is cut off. Alternatively, a biasing member, such as a mechanical spring or an air spring, may apply an upwards biasing force on the coil unit 82 to prevent it from falling downwards, or a counterweight can be provided to counter the force of gravity acting downwards on the coil unit 82.

The upper and lower clamps 85, 95 may have any structure which enables them to grasp and release the biopsy needle 15. In the present embodiment, each clamp comprises a plurality of blocks, each having a surface which can contact the outer surface of the biopsy needle 15 and with the blocks of a clamp being moveable relative to each other to adjust the force with which the blocks are pressed against the needle 15. The upper clamp 85 includes two stationary blocks 86 mounted on a frame 83 secured to the coil unit 82 of the linear actuator 80 and each having a recess 87 for receiving the needle 15. Another block 88 also having a recess 89 for receiving the needle 15 is supported for movement towards and away from the stationary blocks 86 in a direction transverse, e.g., perpendicular to the axis of the needle 15. The movable block 88 can be moved by any suitable actuator. In the present embodiment, the movable block 88 is moved by a rotary electric motor 90 which rotates a lead screw 92 through a right angle gear box 91, the motor 90 and the gear box 91 being mounted on the frame 83. The lead screw 92 engages with an unillustrated nut disposed inside the movable block 88 or with threads formed directly in the block 88. The movable block 88 engages with the frame 83 so as to be capable of moving in the lengthwise direction of the lead screw 92 while being prevented from rotation with the lead screw 92. For example, the movable block 88 may be formed with a projection which slidably engages an elongated groove formed in the frame 83. Rotation of the motor 90 in one direction moves the movable block 88 towards the stationary blocks 86 to grasp the needle 15, while rotation of the motor 90 in the opposite direction moves the movable block 88 away from the stationary blocks 86 and from the needle 15 to release the needle 15. The lower clamp 95 has a structure similar to that of the upper clamp 85. It includes two stationary blocks 96, each having a recess 97 for receiving the needle 15 and each secured to a portion of the second frame 74. A movable block 98 having a recess 99 formed therein for receiving the needle 15 can be moved towards and away from the stationary blocks 96 by a rotary motor 100 which rotates a lead screw 101 engaging with an unillustrated nut disposed in the movable block 98 or with threads formed directly in the block 98. The movable block 98 may be prevented from rotation with the lead screw 101 while being permitted to translate in the lengthwise direction of the lead screw 101 by a projection formed on the movable block 98 which slidably engages with an elongated groove formed in the second frame 74 or by similar structure. When the motor 100 is rotated in one direction, the movable block 98 is moved towards the stationary blocks 96 to clamp the needle 15 between the blocks 96, 98, and when the motor 100 is rotated in the opposite direction, the movable block 98 is moved away from the stationary blocks 96 to release the needle 15. Depending upon the position of the movable blocks with respect to the stationary blocks, each clamp 85, 95 can tightly grasp the needle 15, can completely release the needle 15, or can loosely grasp the needle 15 to permit the needle 15 to slide through the clamp when an axial force above a certain level is applied to the needle 15 while the clamp still guides the lengthwise movement of the needle 15. Each motor 90, 100 may be equipped with a rotary encoder by means of which the position of the movable block of the clamp (and thus how tightly the clamp is grasping the needle 15) can be determined. Many other mechanisms can be used to sense how tightly the blocks are grasping the needle 15, such as a position sensor which directly senses the positions of the movable blocks, or force sensor, such as strain gauges mounted on one or more of the blocks to sense strains corresponding to forces produced when the blocks grasp the needle 15.

The recesses in the blocks can have any shapes which enable the blocks to grasp the needle 15. In the illustrated embodiment, the recesses are V-shaped notches which form tangential contact with the outer surface of the needle 15. Alternatively, the recesses may have a shape, such as arcuate, similar to the shape of the outer surface of the needle 15, or the recesses may be lined with a resilient material which can conform to the shape of the needle 15.

Figure 4:
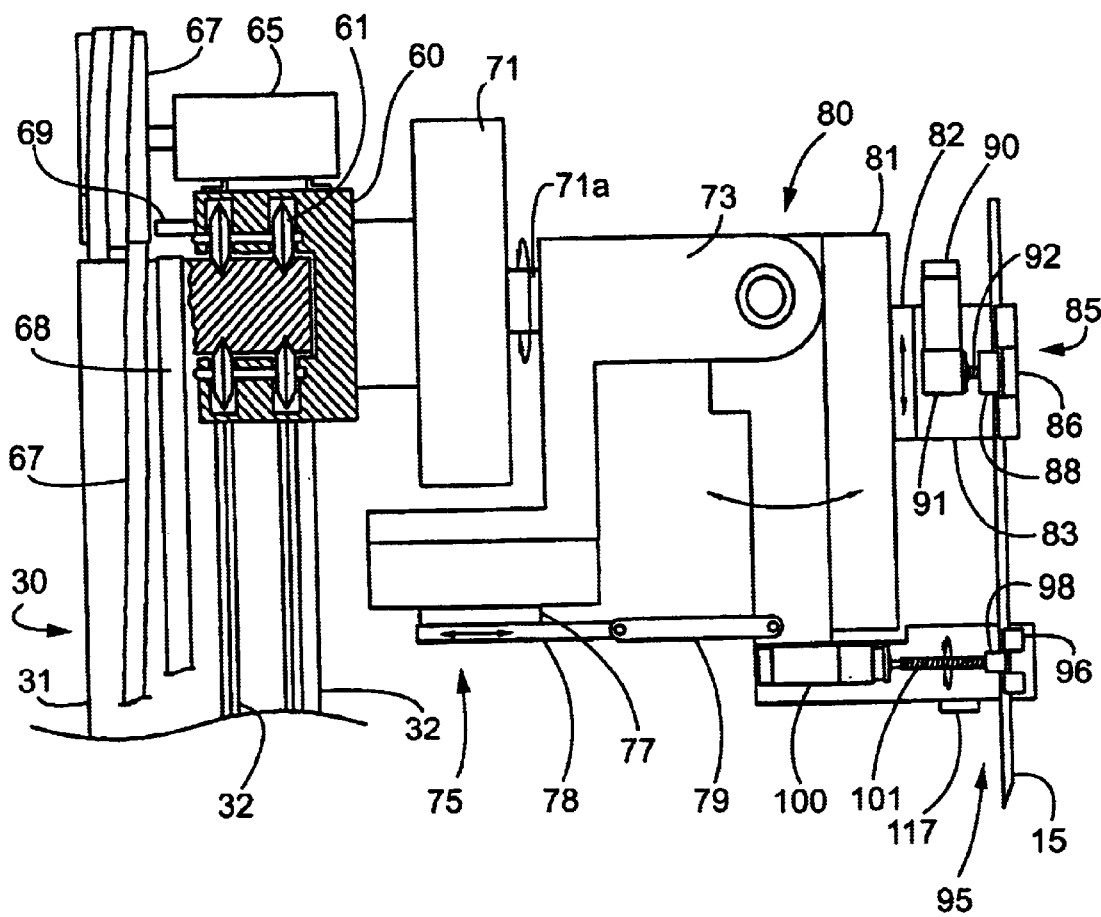
FIG. 4 is an enlarged cutaway view of a portion of FIG. 3.

In order to move a needle 15 downwards FIGS. 3 and 4 to insert the needle 15 into a patient's body, the lower clamp 95 grasps the needle 15 sufficiently loosely for the needle 15 to slide through the lower clamp 95 while the lower clamp 95 acts as a guide for the needle 15, and the upper clamp 85 grasps the needle 15 sufficiently tightly that the needle 15 will not slip through the upper clamp 85 under the resistance to axial movement of the needle 15 expected to be normally encountered during insertion of the needle 15. In this state, the upper clamp 85 is moved by the insertion axis actuator 80 towards the lower clamp 95 to translate the needle 15 downwards by a given distance. After the upper clamp 85 has moved the needle 15 by the given distance, the upper clamp 85 is stopped, the lower clamp 95 grasps the needle 15 sufficiently tightly to prevent the needle 15 from falling, and the upper clamp 85 releases the needle 15. The upper clamp 85 is then moved upwards in the figures by the insertion axis actuator 80 to its initial position. The upper clamp 85 then again grasps the needle 15, the lower clamp 95 loosens its grasp on the needle 15 so as to be able to guide the needle 15 without providing significant resistance to its lengthwise movement, and the above-described process of the upper clamp 85 moving towards and away from the lower clamp 95 is repeated as many times as necessary to insert the needle 15 a desired distance. The needle 15 can be moved upwards in FIGS. 3 and 4 to retract the needle 15 from a patient's body by the reverse of the procedure described above. Namely, with the lower clamp 95 loosely grasping the needle 15 so as to function as a guide, the upper clamp 85 tightly grasps the needle 15 and is moved by the insertion axis actuator 80 upwards away from the lower clamp 95. When the upper clamp 85 reaches the end of its upwards movement, the lower clamp 95 grasps the needle 15 sufficiently tightly to prevent the needle 15 from falling, the upper clamp 85 releases the needle 15, and the insertion axis actuator 80 moves the upper clamp towards the lower clamp 95 to start a new cycle.

The insertion mechanism is shown being used with a rigid medical tool, such as a needle 15, but the insertion mechanism can also be used to insert a flexible tool, such as a catheter, into a patient's body. With a flexible tool, the separation between the upper and lower clamps 85, 95 during insertion of the flexible member can be selected to be sufficiently short that the portion of the flexible tool between the two clamps will not buckle when subjected to a compressive force by the upper clamp 85 moving towards the lower clamp 95.

The insertion mechanism may be equipped with a force sensor for sensing the resistance in the axial direction experienced by the needle 15 during insertion. For example, a strain gauge can be mounted on the coil unit 81, the frame 83, or other member to sense strains resulting from axial forces acting on the needle 15. Alternatively, the current applied to the coil unit 81 of the insertion axis actuator 80 can be measured as an indication of the axial force being exerted on the needle 15 by the coil unit 81. The information obtained by force sensing can be used in various ways, such as to provide force feedback to the operator of the manipulator, or to perform force control of the needle 15.

Figure 6:
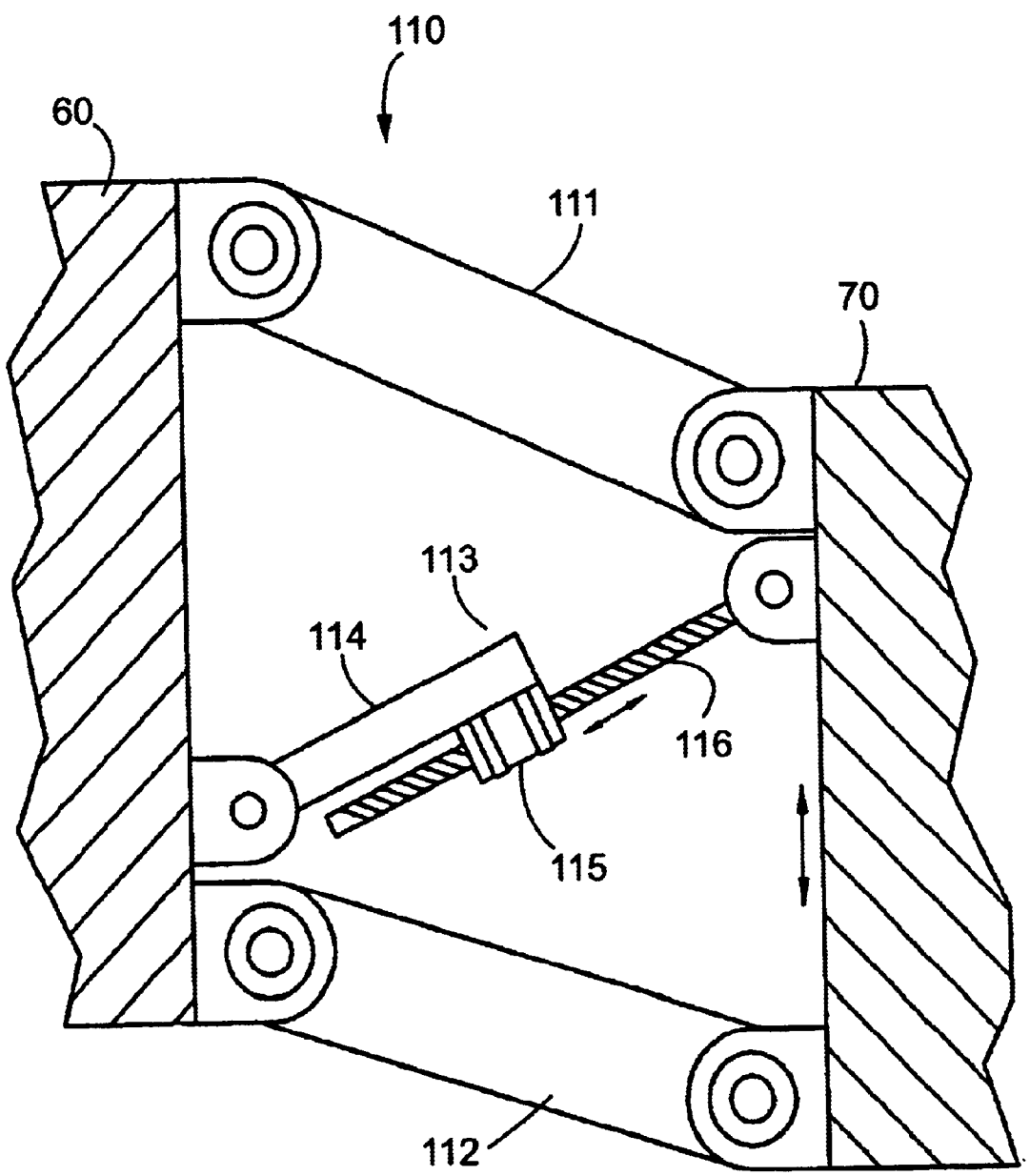
FIG. 6 is a schematic side elevation of a height adjusting mechanism which can be employed in a manipulator according to the present invention.

During insertion of the needle 15 into a patient's body, if the lower clamp 95 is too far away from the patient's body, the portion of the needle between the lower clamp 95 and the patient's body may bend and deviate from the desired path of insertion. The accuracy with which the path of the needle 15 can be controlled can be enhanced by disposing the lower clamp 95 close to the point of insertion into the patient's body to minimize bending of the needle, and the lower clamp 95 may in fact contact the patient's body. Since patients vary in size and since the distance of a patient's body from the arch 31 may vary around the patient's body, the manipulator may be equipped with a mechanism for adjusting the distance of the lower clamp 95 from a patient's body so that the lower clamp 95 can automatically be maintained at a desired distance from at which good control of the path of the needle 15 can be obtained. FIG. 6 illustrates a portion of an embodiment according to the present invention equipped with such a mechanism. The overall structure of this embodiment may be similar to that of the embodiment of FIG. 1 but further includes a height adjusting mechanism 110 disposed between the carriage 60 and the insertion mechanism 70 for adjusting the height with respect to the patient of the entire insertion mechanism 70. The height adjustment mechanism 70 includes first and second parallel links 111 and 112 of equal length, each having one end pivotably connected to the carriage 60 and another end pivotably connected to a portion of the positioning mechanism 70 and together forming a parallel link mechanism. An adjustable length link 113 extending transversely to the first and second links 111, 112 has one end pivotably connected to the carriage 60 and another end pivotably connected to the positioning mechanism 70. When the length of the adjustable length link 113 is varied, the distance of the positioning mechanism 70 from the carriage 60 is varied to change the height of the positioning mechanism 70, while the first and second parallel links 111, 112 maintain the orientation of the positioning mechanism 70 with respect to the carriage 60 constant. The length of the adjustable length link 113 can be adjusted manually or by an actuator. In the present embodiment, the adjustable length link 113 includes a bar 114 having one end pivotably connected to the carriage 60 and having an electric motor 115 with a hollow rotor mounted at its opposite end. An unillustrated nut is mounted inside the rotor of the motor 115, and a lead screw 116 having one end pivotably connected to the positioning mechanism 70 engages with the nut. When the motor 115 is operated, the rotor is rotated with respect to the exterior of the motor 115, and the engagement between the nut and the lead screw 116 causes the lead screw 116 to move further into or out of the motor 115 to adjust the length of the link 113. The motor 115 can be controlled in response to commands from a human operator, or it can be automatically controlled to maintain the lower clamp 95 at a constant distance from a patient's body. For example, a distance sensor 117 can be mounted on some portion of the positioning mechanism 70 (such as on the second frame 74 in FIG. 4) at a known distance from the lower clamp 95 to sense the distance from a patient's body. The output signal from the distance sensor 117 can be input to a controller, which can control the motor 115 to maintain the lower clamp 95 at a desired distance from the patient's body. One example of a distance sensor 117 which can be employed is an ultrasonic distance sensor, but any other type small enough to be mounted on the positioning mechanism may be employed. A motor and a lead screw are just one of many possible mechanisms for adjusting the length of a link of a height adjusting mechanism. Examples of other mechanisms which can be employed include pneumatic or hydraulic cylinders, linear motors, rack and pinion arrangements, and hand-turned adjustment screws. Furthermore, the height of the positioning mechanism 70 with respect to the carriage 60 can be adjusted by devices other than a parallel link mechanism. Having the motor 132 for driving the carriage 130 disposed within the carriage 130 rather than on top of it enables the inner diameter of the guide 120 to be increased without any increase in the overall outer diameter of the manipulator. Increasing the inner diameter of the guide 120 without increasing the overall diameter of the manipulator is desirable because it provides more space for the guide 120 to pass over a patient or permits the manipulator to be used with larger patients. The motor 132 is also better protected against damage when disposed inside the carriage 130.

The insertion mechanism is not restricted to use with a manipulator according to the present invention and may be used with any other type of support mechanism. For example, they may be installed in a fixed location, within a CT machine or other imaging device.

Figure 7:
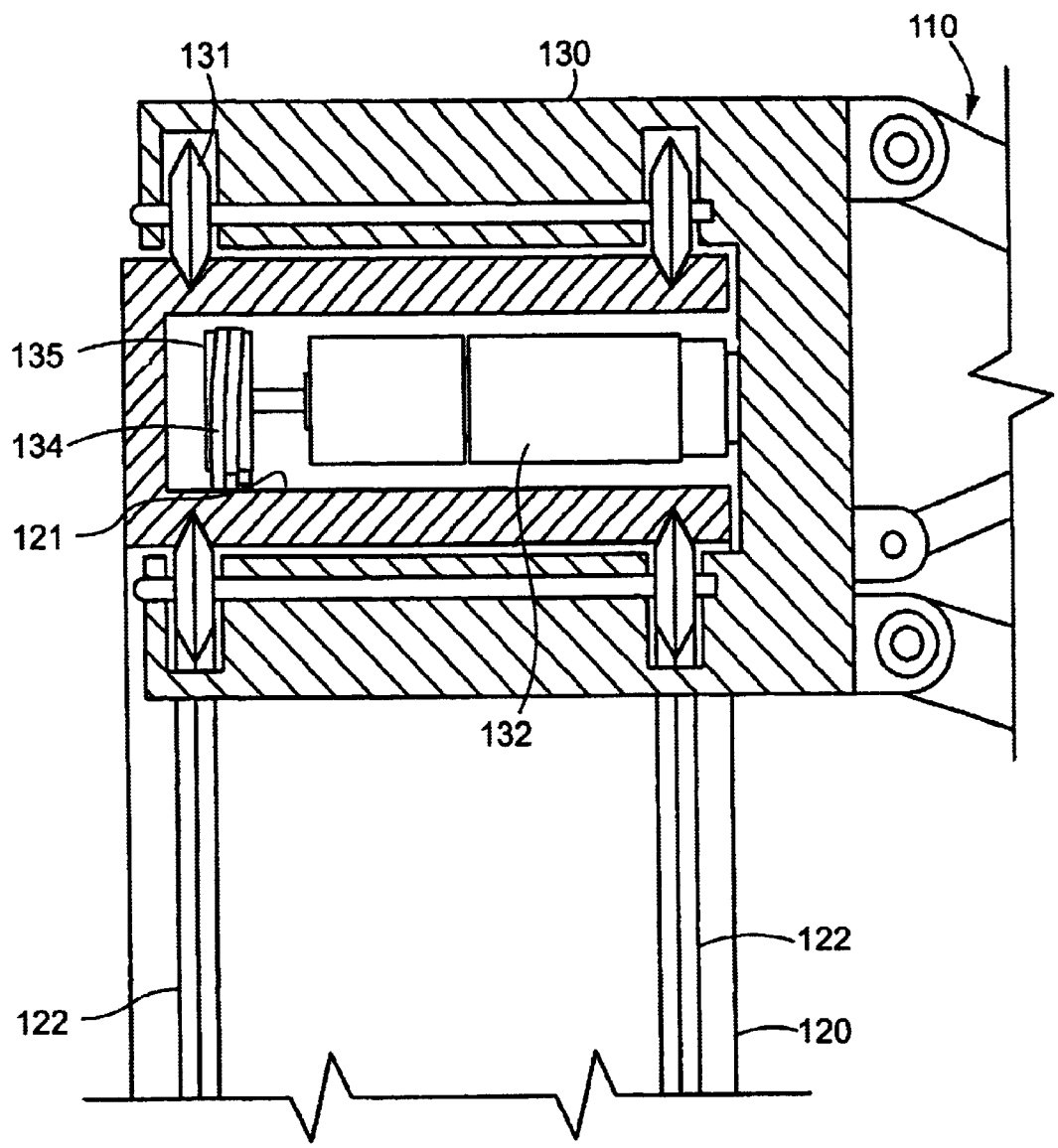
FIG. 7 is a schematic side elevation of a portion of another embodiment of a manipulator according to the present invention.

FIG. 7 illustrates a portion of another embodiment of a manipulator according to the present invention. In this embodiment, the arch 120 of a guide has a generally U-shaped transverse cross section defining a recess 121 which opens onto a side surface of the arch 120. The guide may be otherwise identical to the guide 30 of the embodiment of FIG. 1. A carriage 130 similar to the carriage 60 of the embodiment of FIG. 1 is equipped with wheels 131 which can roll along corresponding grooves 122 formed in the radially inner and outer periphery of the arch 120. The carriage 130 is also equipped with a motor 132 and a capstan 133 driven by the motor 132 which correspond to the motor 65 and the capstan 66, respectively, of the embodiment of FIG. 1. The motor 132 is mounted within the recess in the carriage 130 through which the arch 120 passes and extends into the recess 121 in the arch 120. An elongated flexible member 134, such as a belt or a cable, is secured to the arch 120 and extends along the radially inner surface of the recess 121 in the arch 120 and passes around the capstan 133 one or more times. When the motor 132 is rotated, the engagement between the flexible member 134 and the capstan 133 exerts a drive force on the carriage 130 in the circumferential direction of the arch 120 to translate the carriage 130 in the circumferential direction. Any other suitable drive mechanism for moving the carriage 130 along the arch 120, such as those described with respect to the embodiment of FIG. 1, may instead be employed. The structure of the manipulator may be otherwise the same as in the embodiment of FIG. 1.

Figure 8:
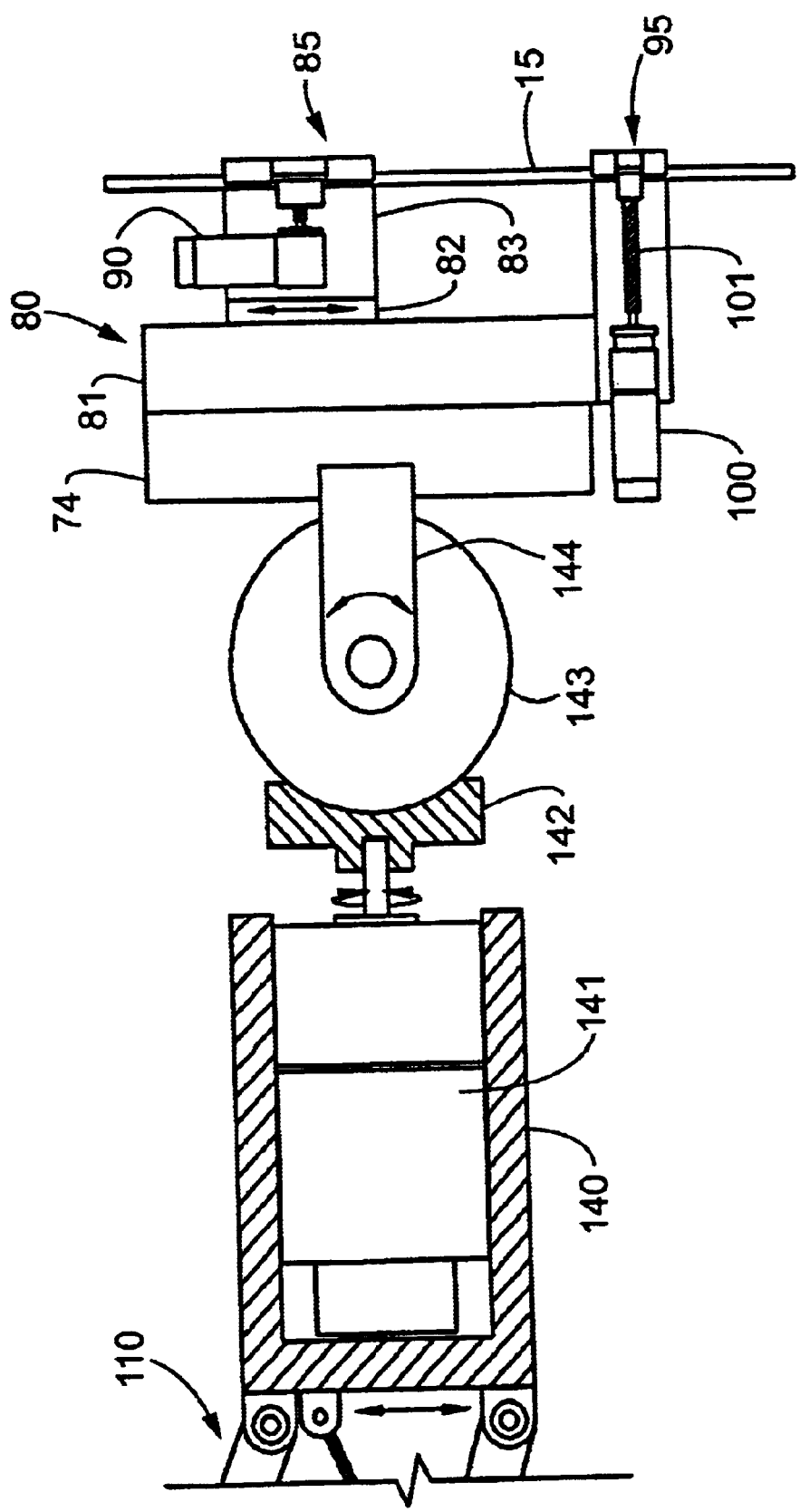
FIG. 8 is a cutaway schematic side elevation of a portion of yet another embodiment of a manipulator according to the present invention.

The pitch angle of the needle 15 can be adjusted by a rotary actuator instead of a linear actuator. FIG. 8 illustrates a portion of another embodiment of a manipulator according to the present invention in which a positioning mechanism includes a rotary motor 143 for adjusting the pitch angle. The rotary motor 143 has a stator surrounding a rotor. The stator is secured to a cradle 142 which is mounted on the output shaft of a yaw motor 141 for producing yawing motion mounted in a frame 140. The rotor of motor 143, which in FIG. 8 extends perpendicular to the plane of the drawing, is secured by a yoke 144 to a frame 74 for supporting an insertion axis motor 80. The structure of this embodiment may be otherwise the same as that of any of the preceding embodiments.

Figure 9:
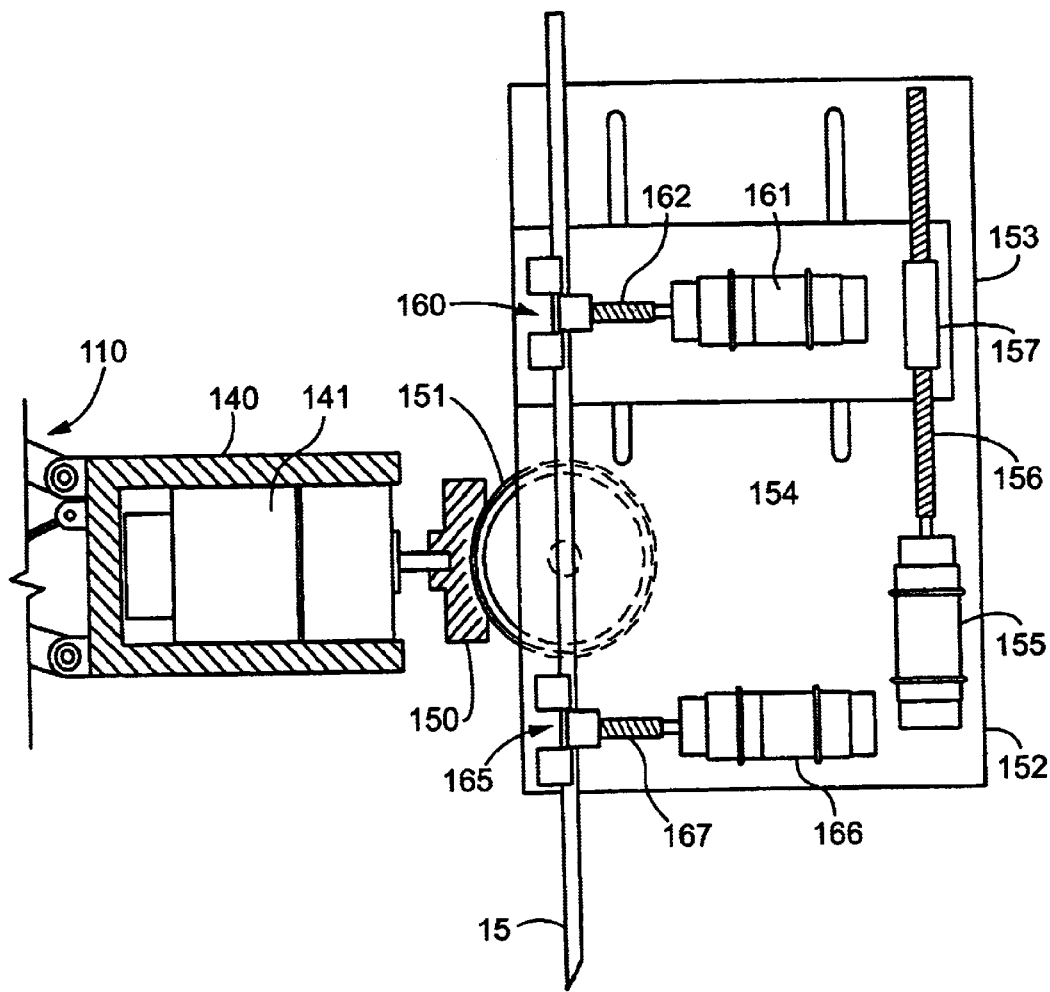
FIG. 9 is a cutaway schematic side elevation of a portion of still another embodiment of a manipulator according to the present invention.
Figure 10:
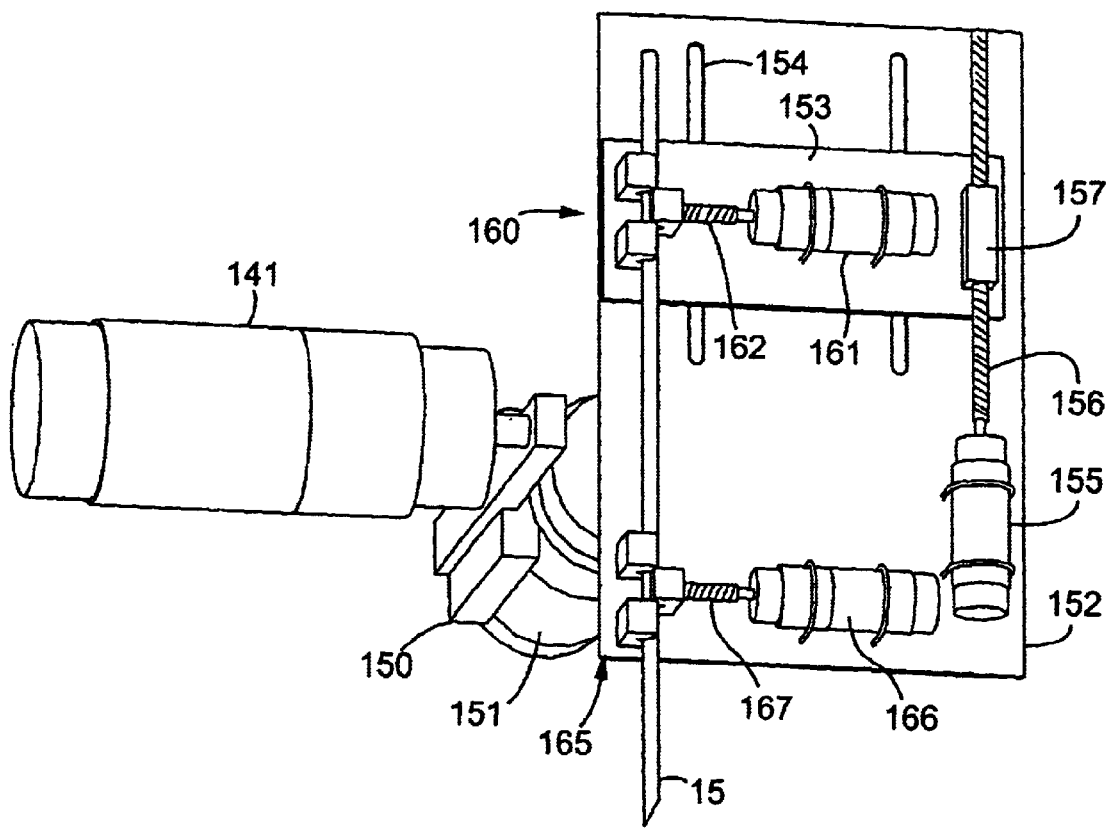
FIG. 10 is a schematic isometric view of the portion illustrated in FIG. 9.
Figure 11:
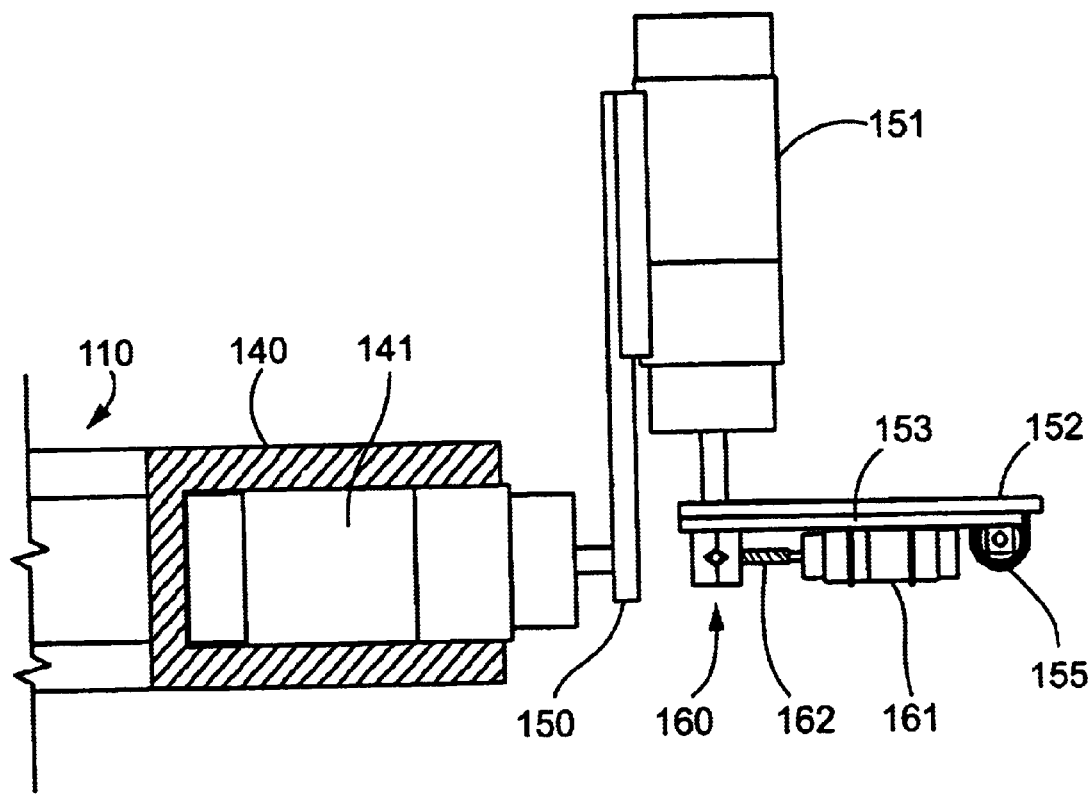
FIG. 11 is a top view of the portion illustrated in FIG. 9.

FIGS. 9–11 are respectively a side elevation, and isometric view, and a top view of a portion of another embodiment of a manipulator according to the present invention employing a positioning mechanism different from that of the preceding embodiments. This positioning mechanism includes a yaw motor 141, a pitch motor 151 supported by the yaw motor 141 for rotating about a yaw axis, and an insertion mechanism for supporting a needle 15 supported by the pitch motor 151 for rotation about a pitch axis. The yaw axis and the pitch axis preferably intersect each other at right angles, and the needle 15 supported by the insertion mechanism preferably has a longitudinal axis passing through the point of intersection between the yaw and pitch axes. The yaw and pitch motors 141, 151 may be of any desired type. For example, in the present embodiment, each motor is a brushless DC motor equipped with a harmonic drive gear train, a harmonic drive being advantageous because it is compact, efficient, and has no backlash, but other types of gear trains can be used, or a gear train can be omitted if the motor has sufficient torque. In addition to providing torque amplification, which permits the use of smaller, lighter, less expensive motors, a gear train can prevent the motor from being backdriven when power to the motor is cut off. A decrease in the weight of the motors is particularly advantageous because it improves the responsiveness and controllability of the positioning mechanism. If desired, each motor may be equipped with an encoder by means of which the yaw and pitch angles of the needle 15 can be determined. If the encoder directly senses rotation of the motor, the provision of a gear train on the output shaft of the motor will multiply the accuracy of the encoder in sensing the rotational portion of the member rotated by the gear train by the reduction ratio of the gear train.

The insertion mechanism includes an upper clamp 160 and a guide in the form of a lower clamp 165 which may be identical in structure to the upper and lower clamps 85, 95 of the embodiment of FIG. 1. The upper clamp 160 can be moved towards and away from the lower clamp 165 in the lengthwise direction of the needle 15 by an insertion axis actuator. In the present embodiment, instead of a linear motor, a rotary motor 155 connected to a lead screw 156 is used as an insertion axis actuator. The lead screw 156 engages a nut 157 secured to a frame 153 supporting the upper clamp 160. When the lead screw 156 is rotated by the motor 155, the frame 153 and the upper clamp 160 are translated in the lengthwise direction of the lead screw 156 towards or away from the lower clamp 165. The motor 155 may be equipped with a gear train for torque amplification and/or an encoder for sensing the position of the upper clamp 160 with respect to the lower clamp 165. While it may be more difficult to perform force control of the needle 15 using a rotary motor and a lead screw as an insertion axis actuator than when using a linear motor, since a lead screw is generally not backdrivable, the upper clamp 160 will remain stationary when electrical power to the motor 155 is cut off, so there is no need for a brake or a gravity compensation mechanism for the upper clamp 160 to prevent the upper clamp 160 from falling down.

The length of a needle required for a given medical procedure will depend upon the location within the body of a patient into which the needle needs to be inserted as well as on the size of the patient. For example, a considerably longer needle may be required to reach a given organ in an obese patient than a in thin patent. If the needle required for a given procedure exceeds a certain length, it may be impossible to introduce the needle while held by the insertion mechanism into the bore of the gantry of a CT machine because of inadequate clearance.

Figure 12:
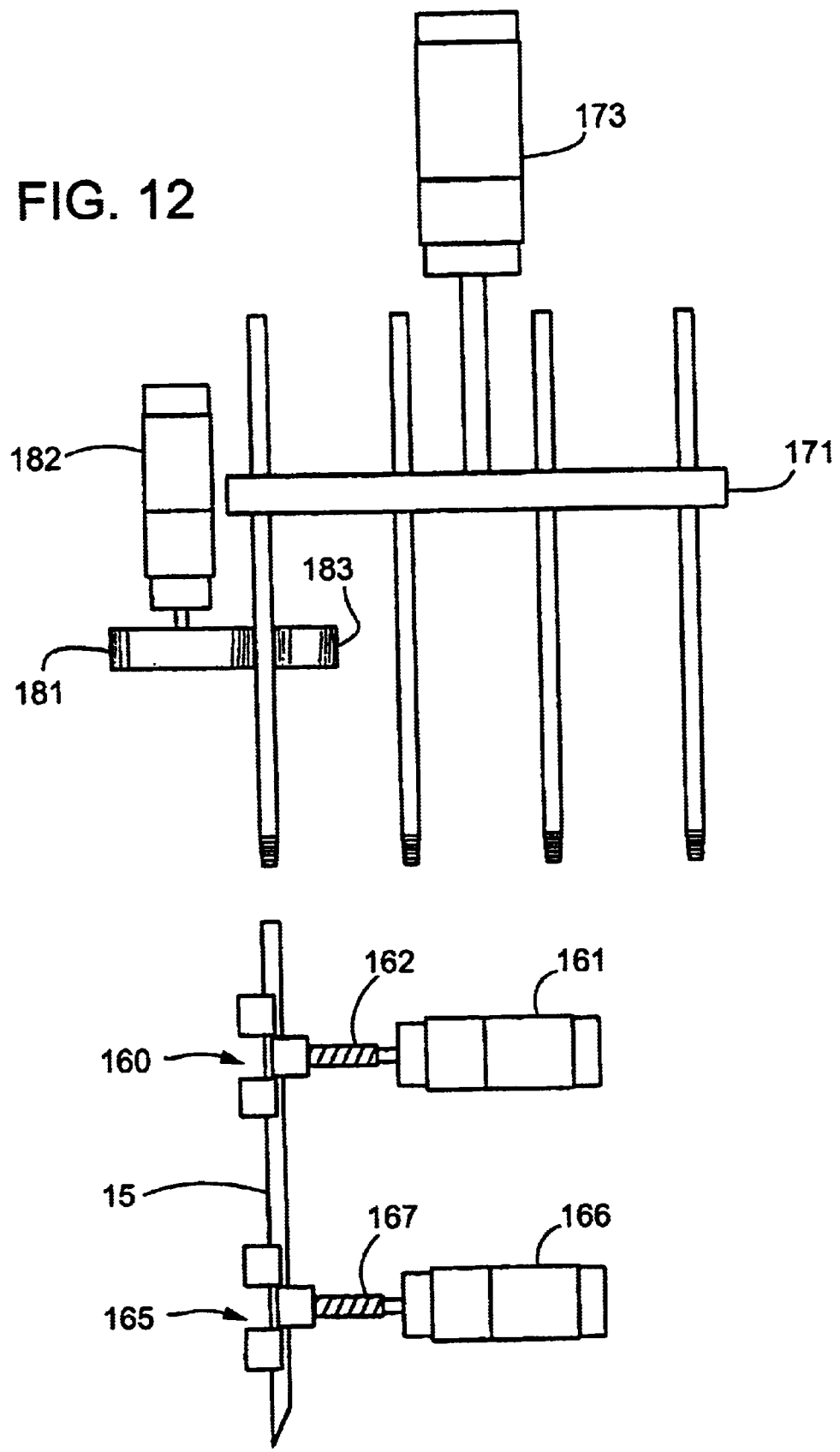
FIG. 12 is a schematic side elevation of a mechanism for assembling a needle from a plurality of needle sections.
Figure 13:
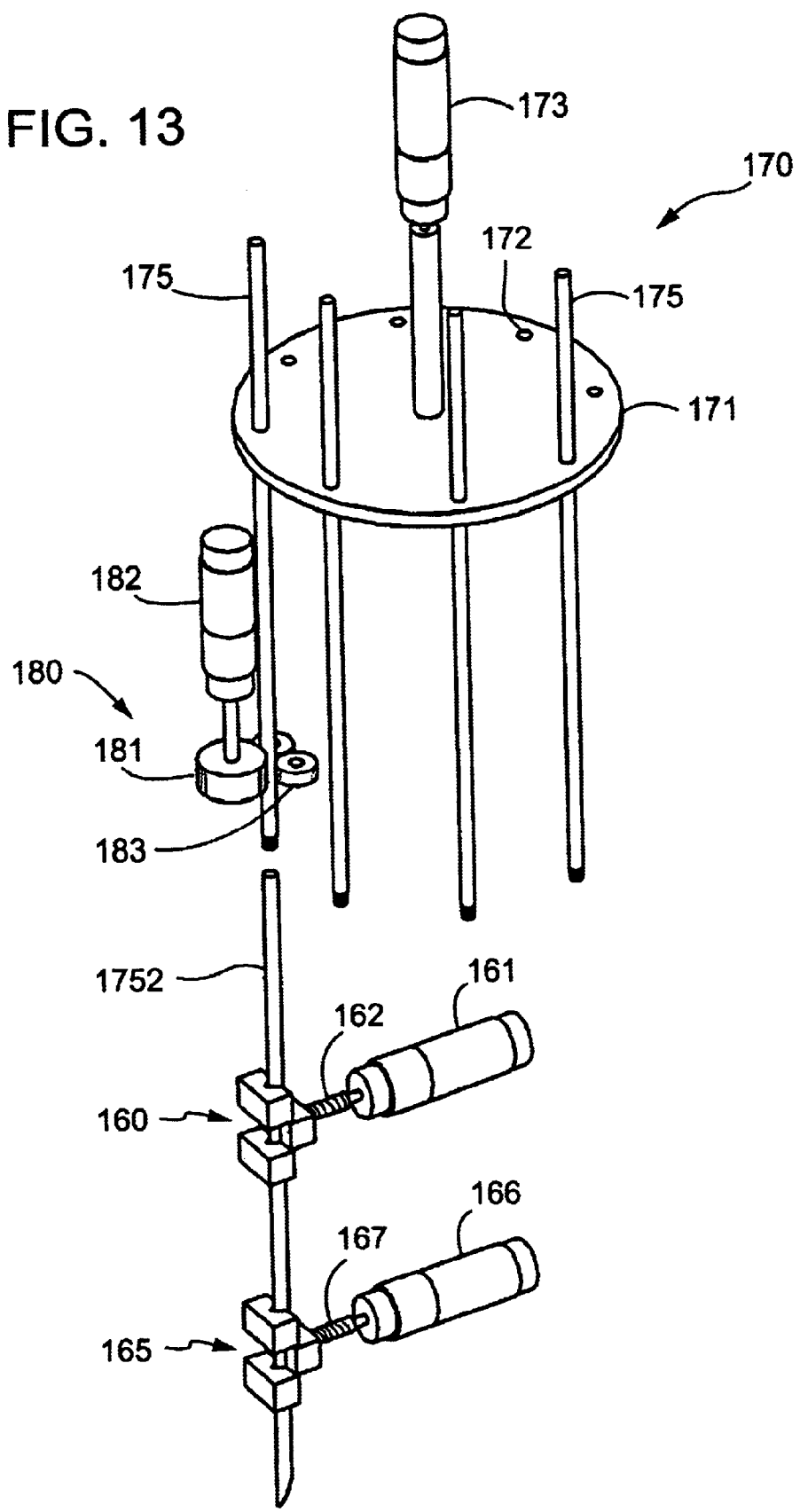
FIG. 13 is a schematic isometric view of the mechanism shown in FIG. 12.

This problem can be overcome by a needle according to the present invention which can be assembled inside a CT machine or other imaging device from a plurality of sections, each shorter than the assembled needle. In an assembled state, the needle sections take up very little space so create no impediment to entry of the manipulator into the-gantry of a CT machine. Further, because it is possible to assemble a needle of any desired length from the needle sections, it is unnecessary to stockpile a large number of needles of different lengths. FIGS. 12 and 13 schematically illustrate a portion of a manipulator according to the present invention equipped with an apparatus for assembling a needle from a plurality of sections. The assembly apparatus includes a supply section 170 for supplying a plurality of needle sections 175 one by one to a position in which they can be joined to each other, and a joining mechanism 180 for joining the needle sections 175 together to assemble a needle. The needle sections 175 can be joined to each other in a variety of ways, such as by a threaded connection, a snap fit, a press fit, or a bayonet fit. In the present embodiment, each needle section 175 has a threaded end which can be engaged with a threaded end of an adjoining needle section 175 by rotation of the two needle sections 175 in opposite directions with respect to each other in a manner similar to the way sections of threaded pipe can be connected to each other. For example, a needle section 175 may have a male thread at one of its lengthwise ends and a female thread at its other lengthwise end which can be engaged with the male thread of an adjoining needle section 175. Tapered threads are preferred for ease of engagement. The needle sections 175 need not be identical. For example, they may include a needle section 175a having a thread at only one of its ends and having its opposite end shaped for piercing the body wall of a patient. Any number of needle sections 175 can be assembled end to end in this manner to obtain a biopsy needle of a desired length. If the method of connecting the needle sections to each other is reversible, an assembled needle can be disassembled into individual needle sections 175 as the needle is being withdrawn from a patient's body.

The illustrated needle supply section 170 comprises a rotary magazine 171 in the form of a plate rotatable by a motor 173 about an axis. The magazine 171 has a plurality of holes 172 formed therein, and a needle section 175 can be held in each hole by friction. The magazine 171 can be rotated to bring each needle section 175 held by the magazine 171 into alignment with the clamps 160, 165 of the needle insertion mechanism. The joining mechanism 180 for joining the needle sections 175 together comprises an elastomeric drive roller 181 rotated by a motor 182 and one or more idler rollers 183 for providing lateral support to a needle section 175 being contacted by the drive roller 181. One or more of the rollers 181, 183 may be movable in a direction transverse to the needle section 175 to enable the needle section 175 to be positioned between the rollers and then enable the rollers to move into frictional contact with the needle section 175. The frictional engagement between the needle sections 175 and the holes 172 in the magazine 171 is strong enough to prevent the needle sections 175 from falling from the magazine 171 under the force of gravity but weak enough to permit the needle sections 175 to be rotated by the drive rollers 181 while still held by the magazine 171 or to be pulled out of the magazine 171 by the upper clamp of the insertion mechanism.

An example of operating the assembly apparatus is as follows. The magazine 171 is rotated until the lowermost needle section 175a having a tapered lower end is aligned with the upper clamp 160 of the insertion mechanism. The upper clamp 160 is then moved upwards by the insertion axis actuator, the upper clamp 160 grasps the needle section 175a, and then the upper clamp 160 pulls the needle section 175a downwards out of the magazine 171 until the upper end of the needle section 175a is below the lower ends of the other needle sections 175 of the magazine 171. The magazine 171 is then rotated until another needle section 175 is aligned with the needle section 175a held by the upper clamp 160. The lower needle section is moved upwards by the upper clamp 160 until the two needle sections 175a, 175 contact each other. The rollers 181 and 183 are then moved into frictional contact with the needle section 175 and the magazine 171, and the drive roller 181 is rotated to rotate the needle section 175 about its axis and secure it to the lower needle section 175 by the opposing threads of the two needle sections. When the threads of the two needle sections 175a, 175 are engaged far enough with each other, the rollers 181, 183 are moved away from the needle section 175, and the upper clamp 160 is moved downwards to pull the needle section 175 out of the magazine 171 and lower the needle section 175 until its upper end is below the lower ends of the needle sections 175 remaining in the magazine 171. The above process can be repeated to add further needle sections 175 to the assembled needle sections held by the upper clamp 160.

The needle supply section 170 may have shapes other than that shown in FIGS. 12 and 13. For example, it may comprise a spring-loaded cartridge, similar to a magazine of a pistol, which moves the needle sections 175 linearly along a path perpendicular to their lengths into a position aligned with the upper clamp 160 of the insertion mechanism.

Figure 14:
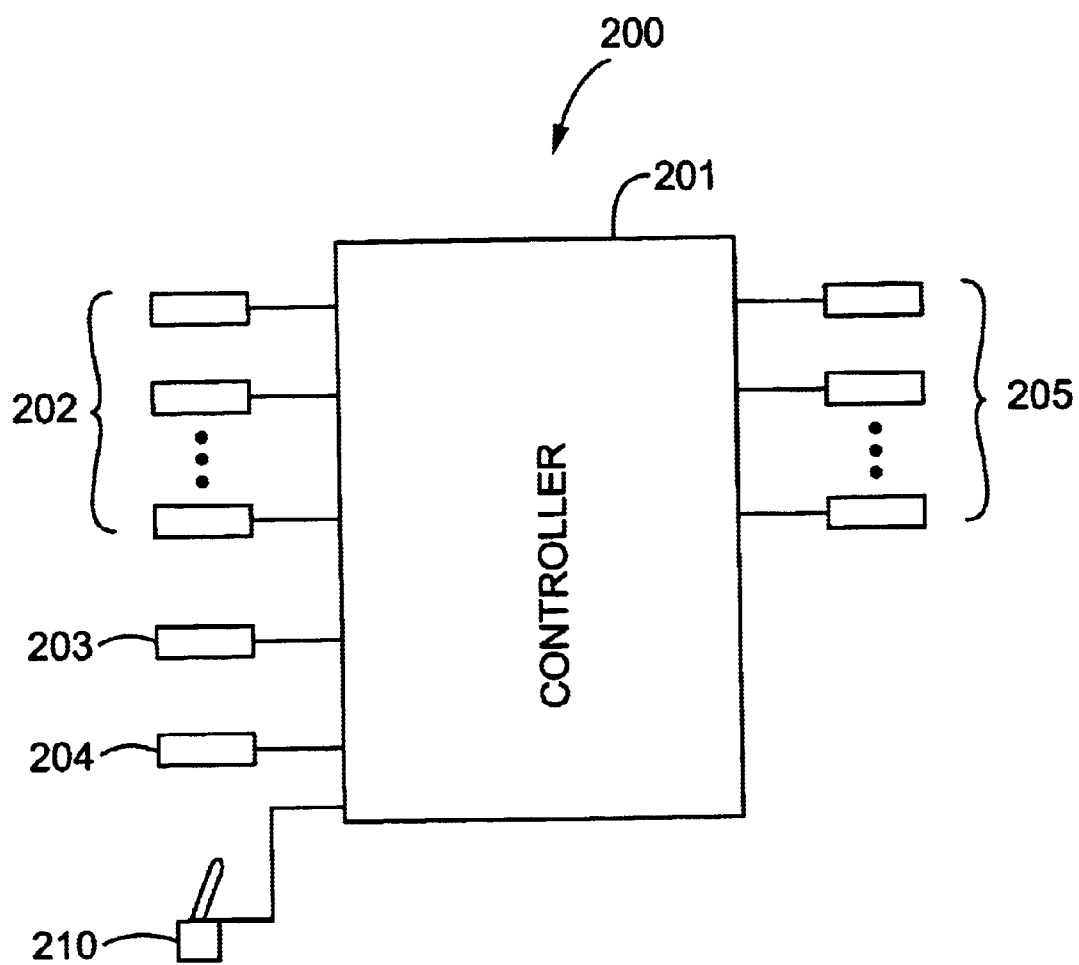
FIG. 14 is a schematic block diagram of a control system which can be employed in the present invention.

A manipulator according to the present invention may be equipped with a control system for controlling the various actuators of the manipulator based on a program or commands from a human operator indicating the desired movements of the manipulator. FIG. 14 is a block diagram of an example of a control system 200 which can be employed with a manipulator according to the present invention. The control system 200 includes an electronic controller 201, such as a general purpose or special purpose microcomputer, which receives input signals from position sensors 202 for various portions of the manipulator, from force sensors 203 (such as strain gauges or current sensors which sense the currents applied to drive motors), from a distance sensor 204, or from other sensing devices. The controller 201 also receives input signals from one or more input devices 210 by means of which the operator can provide the controller 201 with commands indicating the desired movement of the manipulator. A wide variety of input devices 210 can be employed, such as a joystick, a haptic interface (an input device which can provide force feedback to the operator), a keyboard, a foot pedal, a mouse, a digitizer, a computer glove, or a voice-operated controller. The controller 201 may also be equipped with a memory in which commands for controlling the manipulator can be stored to enable the manipulator to operate as a programmed robot rather than as a slave manipulator in a master-slave system. There may be separate input devices 210 for controlling different types of motions of the manipulator, or a single input device can be used to control all operations. Based on input signals from the input devices 210 and the signals from the position sensors 200 and force sensors 203, the controller 201 generates control signals for the actuators 205 so as to move the manipulator in a desired manner.

Figure 15:
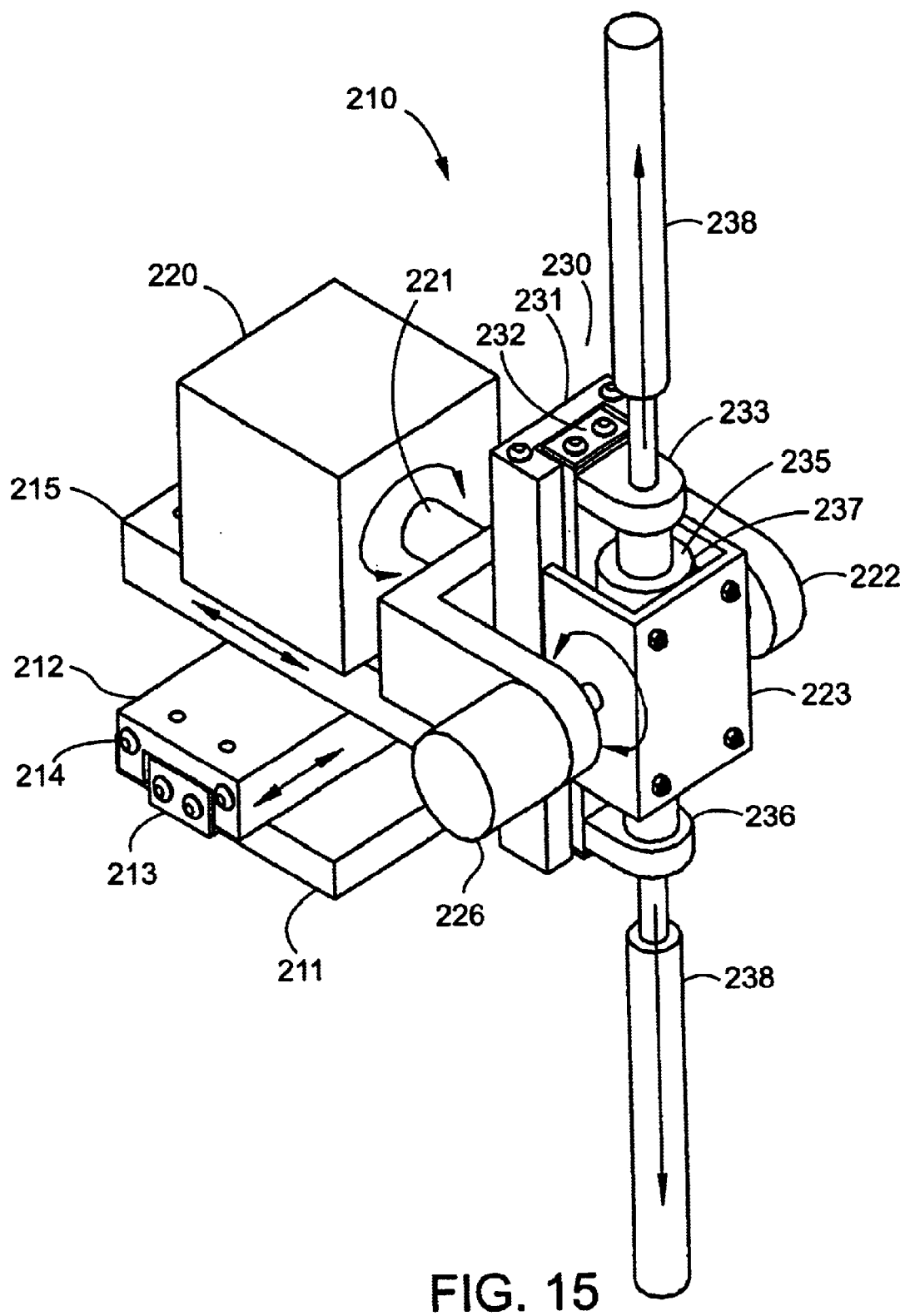
FIG. 15 is a schematic isometric view of an input device for use with the present invention.
Figure 16:
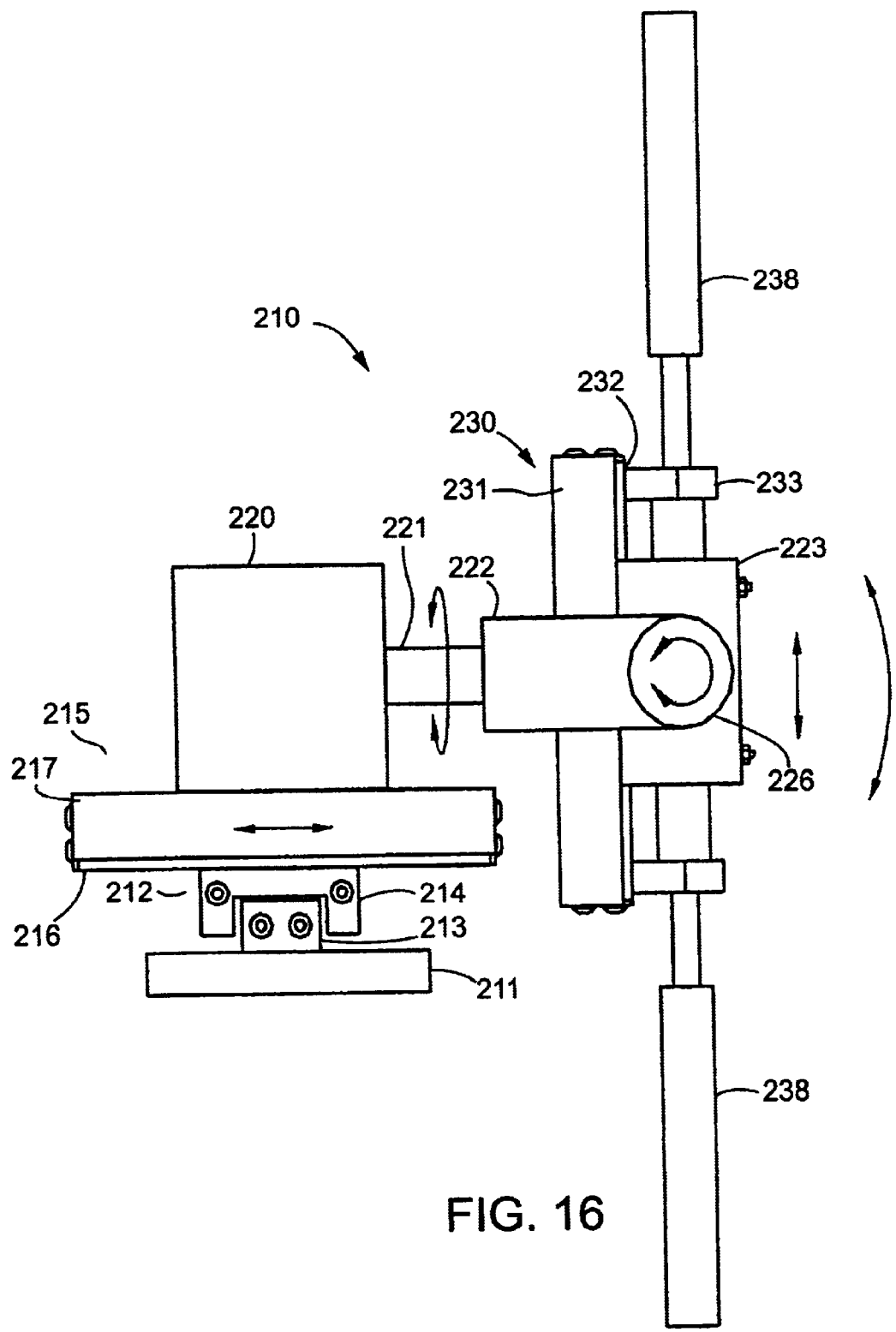
FIG. 16 is a schematic side elevation of the input device of FIG. 15.
Figure 17:
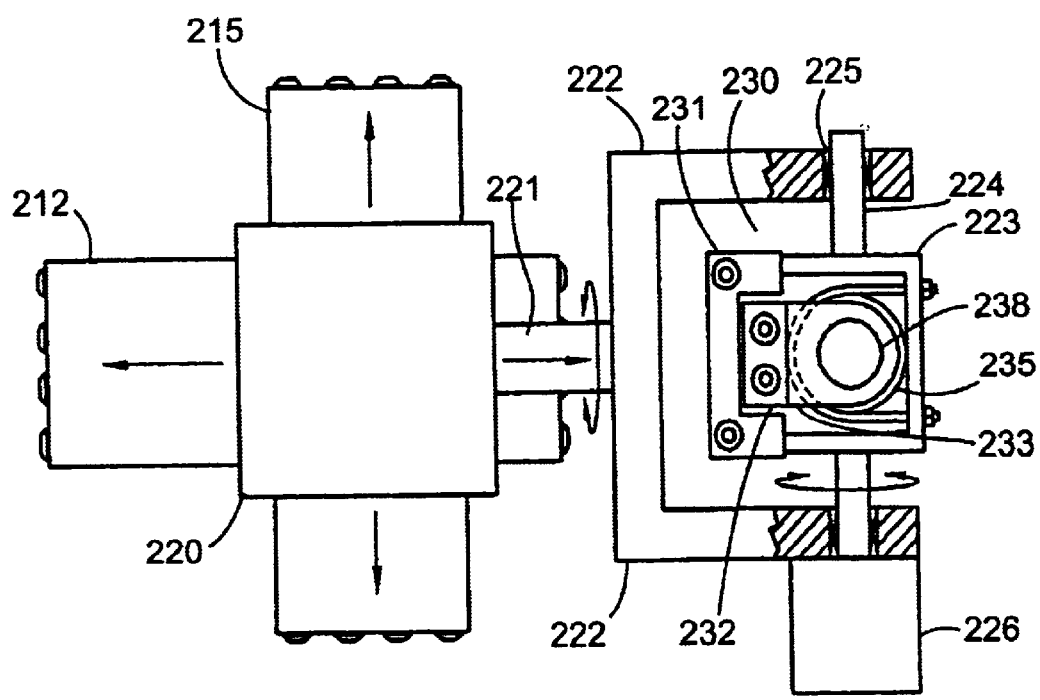
FIG. 17 is a cutaway top view of the input device of FIG. 15.

FIGS. 15–17 illustrate an example of an input device 210 which is particularly suitable for use in the present invention. The input device 210 includes first and second linear guides 212 and 215, such as ball slides, stacked atop each-other transversely (such as at right angles) to each other. The first linear guide 212 has an inner portion 213 secured atop a plate 211 or other support surface and an outer portion 214 slidably disposed on the inner portion 213 for movement in a first direction. The second linear guide 215 has an inner portion 216 secured to the outer portion 214 of the first linear guide 212 and an outer portion 217 slidably disposed on the inner portion 216 for movement with respect to the inner portion 216 in a second direction transverse (such as perpendicular) to the first direction. Each of the guides 212, 215 is equipped with an unillustrated position sensor, such as a linear encoder, for sensing the position of the outer portion of each linear guide with respect to the corresponding inner portion and generating a corresponding output signal which is input to the controller 201. The outer portion 217 of the upper linear guide 215 supports a rotary encoder 220 which senses the rotational position of a shaft 221 about a yaw axis and provides a corresponding output signal to the controller 201. The shaft 221 is secured to a yoke 222 which supports a handle assembly for rotation about a pitch axis perpendicular to the yaw axis. The handle assembly includes a frame 223 having shafts 224 pivotably supported by bearings 225 in the yoke 222 for rotation about the pitch axis. The stationary portion of a linear motor 235 is secured to the frame 223, and the movable portion of the linear motor 235 is secured at its opposite ends to first and second handles 238. The illustrated motor 235 is a brushless linear DC motor having a cylindrical permanent magnet core 236 at its center which is radially polarized and a cylindrical coil unit 227 surrounding the core 226, but other types of linear motor can be employed, as long as the linear motor is backdrivable. The core 236 may be supported entirely by the coil unit 237, but to produce smoother motion and to keep the core 236 better aligned with the coil unit 237, the core 236 may be supported by a linear guide 230 secured to the frame 223. The illustrated linear guide 230 comprises a ball slide having an outer portion 231 secured to the frame 223 and an inner portion 232 secured to the ends of the core 236 by flanges 233 to which the handles 238 are secured. The linear motor 235 or the linear guide 230 may be provided with an unillustrated position sensor, such as a linear encoder, to sense the position of the core 236 in its lengthwise direction. A rotary encoder 26 may be provided on the yoke 222 to sense the angular position of one of the shafts 224 of the frame 223 (and therefore the angular position of the handles 238) about the pitch axis.

The controller 201 receives the output signals from the various encoders 202 and controls the various actuators 205 so as to move the corresponding parts of the manipulator in a direction indicated by the operator. When the input device 210 is used with the embodiment of FIG. 1, for example, if the operator moves the handles 238 so as to move the outer portion of the upper linear guide 245 in the second direction, the guide 30 of the manipulator is moved in the lengthwise direction of the table 20. If the handles 238 are moved in the first direction to move the outer portion 214 of the lower linear guide 212 in the first direction, the motor 65 for the carriage 60 is operated to move the carriage 60 along the arch 31 in the widthwise direction of the table 20. If the handles 238 are rotated about the yaw axis or the pitch axis, the yaw axis motor 71 or the pitch axis motor 76 of the positioning mechanism is operated to yaw or pitch the needle 15. Furthermore, if the handles 238 are moved in their lengthwise direction, the insertion axis motor 80 is operated to move the needle 15 in its lengthwise direction. Operation of the input device 210 is thus highly intuitive in that translations of the handles 238 produce corresponding translations of the needle 15 in the same direction, and rotations of the handles 238 produce corresponding rotations of the needle in the same direction. Bearings for supporting the shafts 221, 224 may be selected to provide sufficient friction that the handles 238 will maintain an orientation imparted to them about the yaw or pitch axes against the force of gravity when the operator releases the handles 238. As a result, the operator can determine the orientation of the needle 15 with respect to a patient by observing the orientation of the handles 238 of the input device 210. When the linear motor 235 is activated, it can be controlled to automatically maintain the position of the handles 238 constant in the lengthwise direction against the force of gravity when the operator releases them. The linear motor 235 may be equipped with a brake mechanism which is automatically actuated when power to the linear motor 235 is cut off, a counterweight, a biasing spring, or other gravity compensation system to prevent the handles 238 from falling in the lengthwise direction under the force of gravity at this time.

If desired, the linear motor 235 may be controlled so as to provide force feedback to the hands of the operator holding the handles 238 of the haptic interface, whereby the operator can sense the resistance to insertion encountered by the needle being manipulated. Methods of controlling a master to provide feedback of forces encountered by a slave are well known in the art, and any such methods can be employed to control the linear motor 235 to provide force feedback. Additional actuators can be mounted on the input device 210 to provide force feedback for movements of the handles 238 in directions other than their lengthwise directions or about various axes, but typically the operator is not interested in the resistance to movement of the needle except in its lengthwise direction.

The gain of the control system 200 can be adjusted to enhance the dexterity of the operator of the manipulator. For example, the gain can be set such that movement of the handles 238 of the input device 210 results in much smaller movements (either translational or rotational) of the needle 15. Thus, movements of the handle 238 by the operator on the order of millimeters could be reduced to motions of the needle 15 on the order of micrometers, enabling the operator to make controlled movements of the needle 15 much smaller than he could make by hand. On the other hand, when the needle 15 needs to make large movements, the gain can be set such that movement of the handles 238 of the input device 210 by the operator results in larger translational and/or rotational movements of the needle 15. Scaling up the motions of the handles 238 in this manner permits the operator to maintain his hands relatively stationary in the most comfortable position, which again enhances the operator's dexterity. When the control system 200 provides force feedback to the handles 238 of the input device 210, the gain of the control system 200 may also be adjusted to enhance the operator's sense of touch. For example, the resistance to movement of the input device 210 felt by the hand of the operator holding the handles 238 may be controlled to be greater than the resistance to movement encountered by the needle 15 so that the operator can clearly sense even low levels of resistance encountered by the needle 15. Scaling up the resistance felt by the operator is helpful when the needle 15 is contacting soft tissue. On the other hand, when the needle 15 is contacting bone or other hard materials, it may be desirable to scale down the resistance felt by the operator.

Most individuals experience some level of tremor in their hand motions when performing manual operations. If the control system 200 has a manually operated input device 210, the control system 200 may be equipped with a filter which filters out components of a signal from the input device 210 having the frequency of the tremor so that the tremor is not reproduced in the motions of the needle 15.

Some imaging devices (such as magnetic residence imaging devices) are by their nature generally unable to form an image of a needle in the field of the imaging device. When a manipulator according to the present invention is used with such an imaging device, since an actual image of the needle cannot be displayed for viewing by the operator of the manipulator, a virtual image of the needle may be superimposed upon the image of the patient's body to enable the operator to visualize the position of the needle with respect to the patient's body. The position of any portion of the needle with respect to the manipulator can easily be calculated from the displacements and rotations of the moving portions of the manipulator with respect to reference positions as measured by the various encoders, so if the position of some portion of the manipulator with respect to the portion of the patient's body appearing in an image is precisely known, a virtual image of the needle can be constructed and superimposed on the actual image of the patient. If the position of an image of a region of a patient's body taken with an imaging device is precisely known with respect to the patient's body, a manipulator according to the present invention can be used to manipulate a needle after an image of a patient have been taken and possibly after the patient has been removed from the imaging device. The image data formed by the imaging device are typically capable of being stored in a memory for display at any desired time. The display of the image data can be controlled so that a region in the vicinity of the current position of the tip of the needle is displayed, and a virtual image of the needle can be superimposed on the image of the region of the patient's body. If the operator moves the needle outside the region of the patient's body currently displayed, the region being displayed can automatically be shifted to correspond to the new position of the needle. Thus, to the operator of the manipulator, it appears as though the needle is being inserted into the patient's body while imaging is taking place.

The virtual image of the needle may be similar in shape and size to the actual needle, adjusted to the scale of the image on which it is superimposed, or it may be schematic, with the shape and size of the virtual image modified from those of the actual needle to make the virtual image easier for the operator to see, to reduce the amount of data processing required to display the virtual image, etc.

The ability to view a virtual of a needle on an actual image of a patient's body after imaging has taken place has a number of advantages. The time required to initially process the data obtained by an imaging device so as to form an image may be much longer than the time required to redisplay the image after the data has been processed. The long time needed for the initial processing may make it impractical to view the position of the needle in real time. For example, if it takes twenty minutes to process image data before it can be displayed, the operator of the manipulator must wait twenty minutes before viewing an image of a needle each time he moved the needle. In contrast, if the needle can be inserted into a patient after the completion of imaging and the needle can be manipulated while a virtual image of the needle is superimposed on an actual image of the patient's body, the image of the patient's body and the virtual image of the needle can be updated instantaneously whenever the operator moves the needle. As a result, the length of time for which the needle must be inserted into the patient's body can be greatly reduced compared to when the needle is inserted while imaging is taking place.

Furthermore, if the patient can be removed from the imaging device during manipulation of the needle after imaging has taken place, there will be more room in which the manipulator can operate, enabling the manipulator to be of larger size or to move to locations which might be difficult for the manipulator to reach with the patient still in the imaging device.

Figure 18:
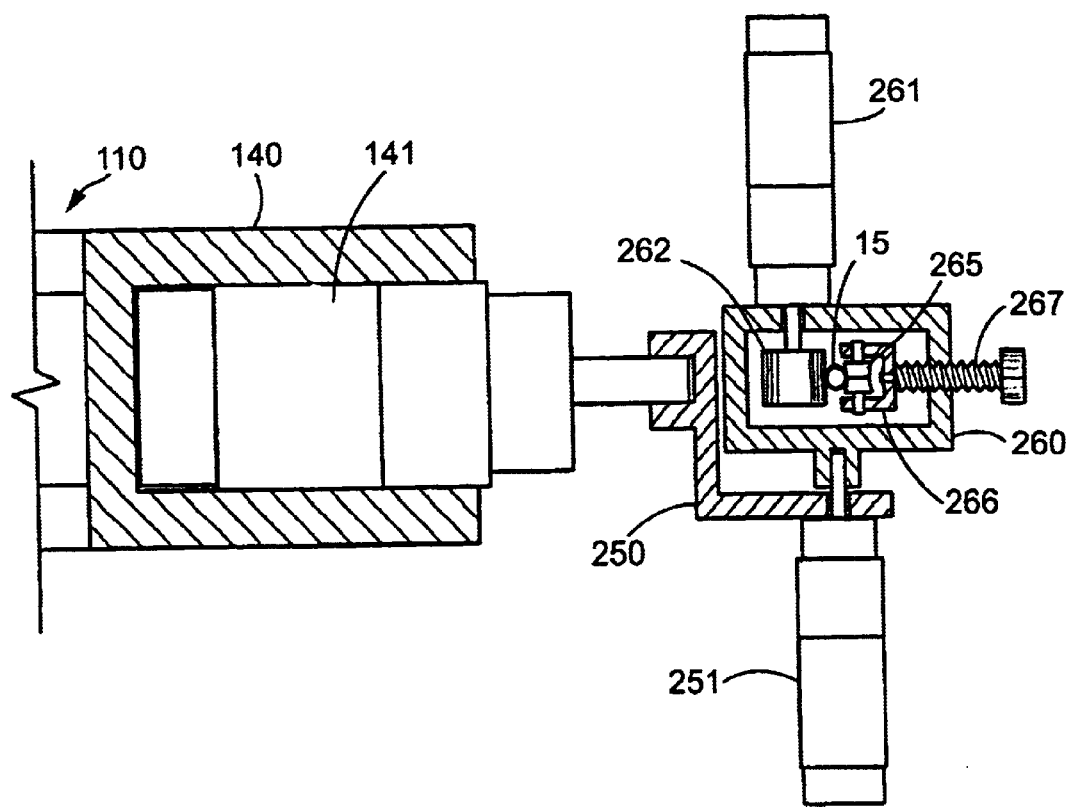
FIG. 18 is a schematic top view of a needle insertion mechanism of another embodiment of a manipulator according to the present invention.
Figure 19:
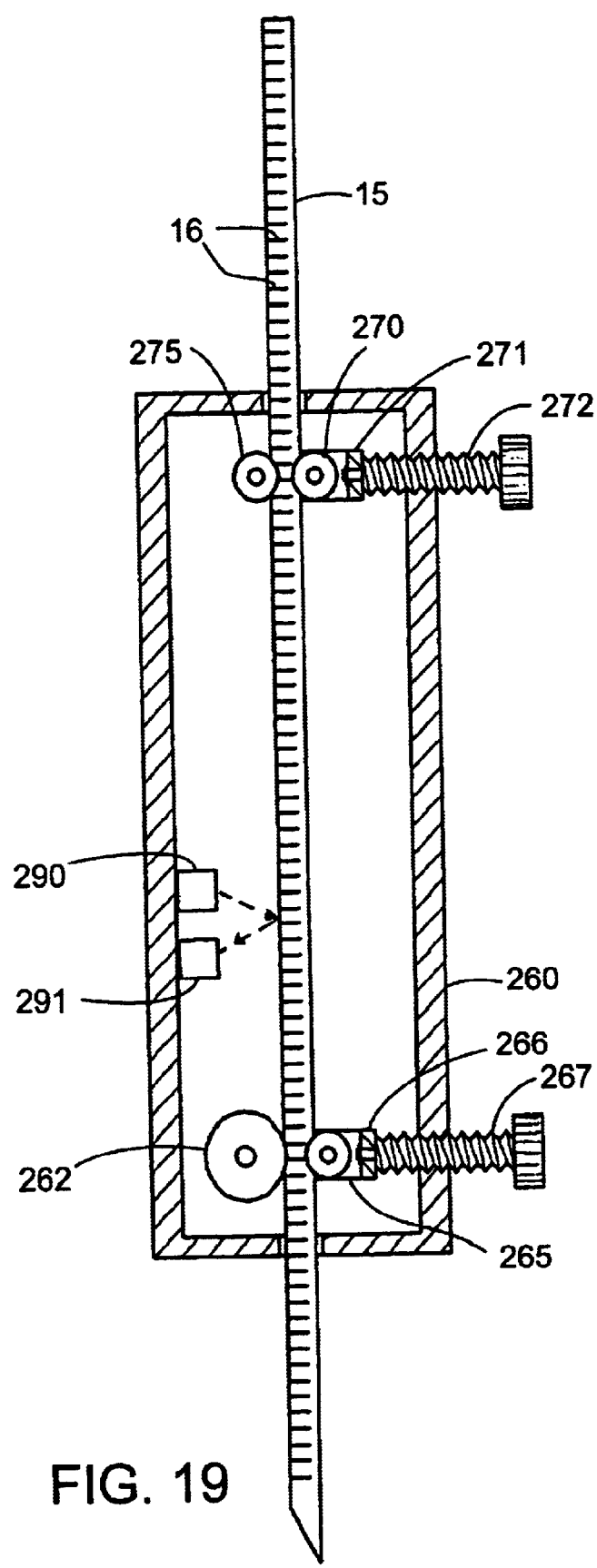
FIG. 19 is a schematic cross-sectional elevation of the needle insertion mechanism shown in FIG. 18.

Forming an image of a patient before a needle is inserted into the patient also enables the definition of boundaries for the path of movement of the needle in the patient's body. There may be regions of the patient's body which it is desirable to avoid, such as blood vessels, nerves, or delicate organs. After an image of a patient has been created by an imaging device and the patient is removed from the imaging device, regions of the image which is desirable to avoid can be identified and marked electronically. Then, when the needle is inserted into the patient's body and the position of the needle is determined, force feedback applied to an input device can be controlled to impede or prevent the operator from moving the needle via the input device to a region to be avoided. For example, when the needle approaches such a region, feedback can be applied to the input device to provide resistance to the hand of the user, with the resistance increasing the closer the needle is to the region to be avoided. A mechanism for inserting a needle into a patient's body is not restricted to one employing clamps which grasp the medical tool. FIGS. 18 and 19 are respectively a schematic top view and a schematic cross-sectional elevation of a portion of an embodiment of a manipulator according to the present invention in which a needle 15 is translated in its lengthwise direction to be inserted into or withdrawn from a patient's body by rolling contact with a roller. As shown in these drawings, a yaw motor 141 which is supported by an unillustrated carriage through a height adjusting mechanism 110 can rotate a first frame 250 about a yaw axis. A pitch motor 251 is mounted on the first frame 250 and has an output shaft secured to a second frame 260 for rotating the second frame 260 about a pitch axis perpendicular to the yaw axis. The yaw axis and the pitch axis preferably pass through the longitudinal axis of the needle 15 so as to minimize lateral movement of the lower end of the needle 15 when it is yawed or pitched. The second frame 260 supports a needle drive motor 261 having an output shaft on which a drive roller 262 is mounted for rolling contact with the needle 15. The second frame 260 also rotatably supports a pressing roller 265 which maintains the needle 15 in rolling contact with the drive roller 262, and a guide comprising a plurality of guide rollers 270, 275, for example, which guide the needle 15 as it moves in its lengthwise direction. The pressing roller 265 is shown positioned directly opposite the drive roller 262, and the guide rollers 270, 275 are spaced from the drive roller 262 in the lengthwise direction of the needle 15. The drive roller 262 may be made of any material which can frictionally engage the needle 15 so as to be in rolling contact with the needle 15, preferably with a minimum of slippage. For example, the drive roller 262 can be made of a resilient material, such as an elastomer, or it may be made of a hard material, such as a hard plastic or a metal. The drive roller 262 may be formed with teeth, knurling, or other form of surface irregularities to increase the coefficient of friction between the drive roller 262 and the needle 15.

The illustrated guide rollers 270, 275 are in rolling contact with the needle 15, but they may instead be in sliding contact, or they may be spaced from the needle 15 so as to be capable of guiding it without contacting it. In the illustrated embodiment, the pushing roller 265 and each of the guide rollers 270, 275 have a V-shaped groove extending around its circumference and engaging with the outer surface of the needle 15 to prevent lateral movement of the needle 15. The drive roller 262 may be formed with a similar groove to position the needle 15.

The positions of one or more of the rollers 262, 265, 270, 275 may be adjustable in a direction transverse to the longitudinal axis of the needle 15 to enable the pressure of the rollers against the needle 15 to be varied or to adjust the spacing between an opposing pair of rollers to enable the rollers to accommodate needles of different diameters. In the present embodiment, the position of the pressing rollers 265 and of one of the guide rollers (such as guide roller 270) of each pair of rollers is adjustable in a direction transverse (such as perpendicular) to the lengthwise direction of the needle 15. The pressing roller 265 is rotatably mounted on a yoke 266 which is supported by an adjusting screw 267 which engages with threads formed in the second frame 260. The inner end of the adjusting screw 267 is rotatably connected to the yoke 266 to enable the yoke 266 to rotate about the axis of the adjusting screw 267, while the outer end of the adjusting screw 267 can be rotated, either manually or by an unillustrated drive mechanism, to advance or retract the adjusting screw 267 and thereby moving the pressing roller 265 closer to or farther from the drive roller 262. In a similar manner, guide roller 270 is rotatably supported on a yoke 271 which is rotatably mounted on the inner end of an adjusting screw 272 which engages threads formed in the second frame 260. When the adjusting screw 272 is rotated, the guide roller 270 is moved closer to or farther from the other guide roller 275. Guide roller 275 may be rotatably supported by the second frame 260 in a fixed location, such as on an unillustrated axle, or it may also be supported so that its position can be adjusted. The drive roller 262 is shown supported in a fixed position with respect to the needle 15, but it may also be supported so that its position transverse to the longitudinal axis of the needle 15 can be adjusted. Various other mechanisms can be employed to adjust the position of the rollers, such as biasing springs or levers which urge the rollers into contact with the needle.

The rotational axes of all four rollers 262, 265, 270, 275 are shown as being parallel to one another, but they need not be. For example, the axes of the guide rollers 270, 275 can be perpendicular or at another angle to the axes of the rollers 262, 265.

The drive motor 261 or one of the rollers in rolling contact with the needle 15 may be equipped with a shaft encoder by means of which the position of the needle 15 in its lengthwise direction may be determined by counting the rotations of the drive motor 261 or the roller.

The drive roller is shown positioned below the guide rollers 270, 275, but it may be positioned above them or between a plurality of pairs of guide rollers.

The needle 15 may be guided by members other than guide rollers. For example, a clamp, such as used in the embodiment of FIG. 8, a plate having a hole through which the needle 15 can loosely pass, or any other member which can resist lateral movement of the needle 15 and thereby control its orientation can be employed.

If desired, the axial force being applied to the needle 15 during insertion may be measured for purposes of performing force feedback to the operator of the input device 210 and/or force control of the needle 15. Some examples of methods which can be employed to sense the axial force include measuring the torque exerted by the shaft on which the drive roller 262 is mounted, measuring the current supplied to the drive motor 261, and measuring forces applied to a member supporting the drive motor 261 with strain gauges.

Figure 20:
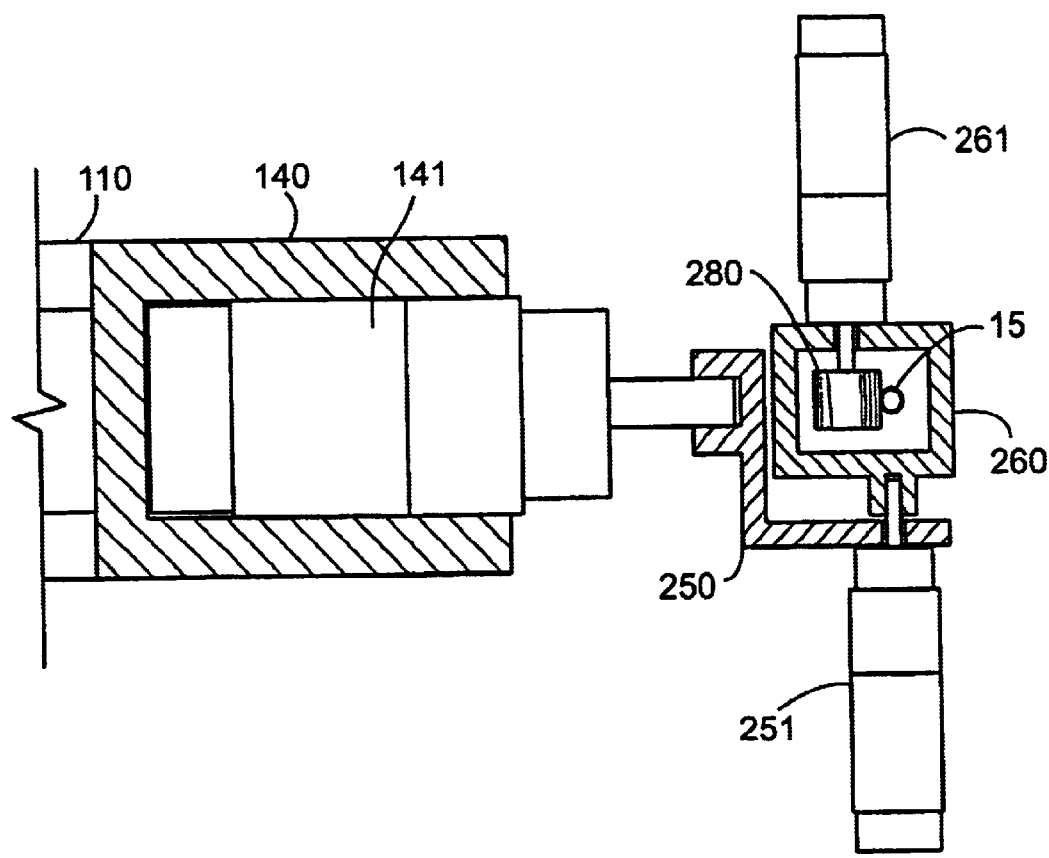
FIG. 20 is a schematic top view of a needle insertion mechanism of yet another embodiment of a manipulator according to the present invention.
Figure 21:
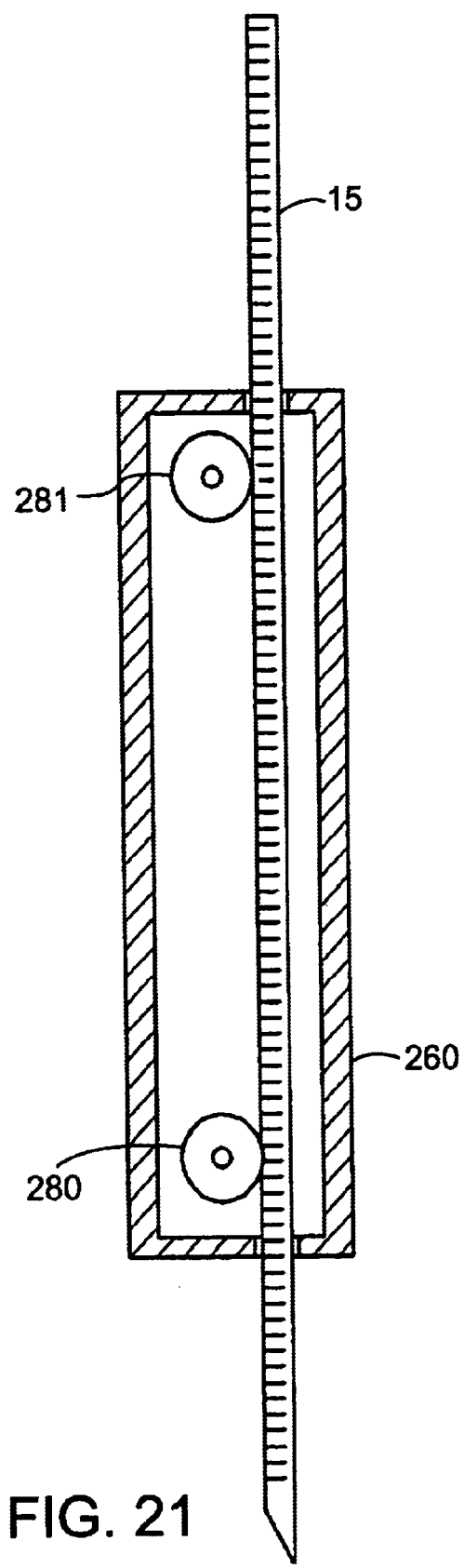
FIG. 21 is a schematic cross-sectional elevation of the needle insertion mechanism of FIG. 20.

FIGS. 20 and 21 are respectively a schematic horizontal cross-sectional view and a schematic cross-sectional elevation of a modification of the embodiment shown in FIGS. 18 and 19. In this embodiment, the pressing roller 265 and one of the guide rollers (such as the guide roller 270 on the right side of the needle in FIG. 18) have been omitted, and the drive roller 262 and the other guide roller 275 have been replaced by a drive roller 280 and a guide roller 281, respectively, which are both magnetically attracted to the needle 15 so that the needle 15 can remain attached to the rollers 280, 281 without the need for any other rollers to press the needle 15 against them. The structure of this embodiment may be otherwise the same as that of the embodiment shown in FIGS. 18 and 19. The magnetic attraction may be attained by magnetizing the rollers 280, 281 and/or the needle 15 or by disposing a magnet in contact with each of the rollers 280, 281 and having the magnets attract the needle 15 through the rollers 280, 281. Each roller 280, 281 may be shaped so as to resist lateral movement of the needle 15 as the needle 15 translates in its longitudinal direction. For example, each of the rollers may have a V-shaped groove extending around its circumference in which the needle 15 can be received. When the drive roller 280 is rotated by the drive motor 261, the drive roller 280, which is in rolling contact with the needle 15, is translated in its lengthwise direction. To reduce slipping between the drive roller 280 and the needle 15, the drive roller 280 may be formed with knurling, teeth, or other surface irregularities to increase its roughness, or a thin layer of an elastomer or other material with a high coefficient of friction may be disposed on the surface of each of the drive rollers 280 in contact with the needle 15, with the layer being sufficiently thin that the needle 15 can remain magnetically attached to the drive roller 280.

The guide roller 281 may also be formed with a surface which minimizes slippage between it and the needle 15,. but because the guide roller 281 serves to guide the needle rather than translate it, it does not matter if there is slippage of the needle 15 with respect to the guide roller 280. For example, the guide roller 280 may be replaced by a stationary guide having a low friction surface which is in sliding contact with the needle 15 rather than rolling contact.

Figure 5:
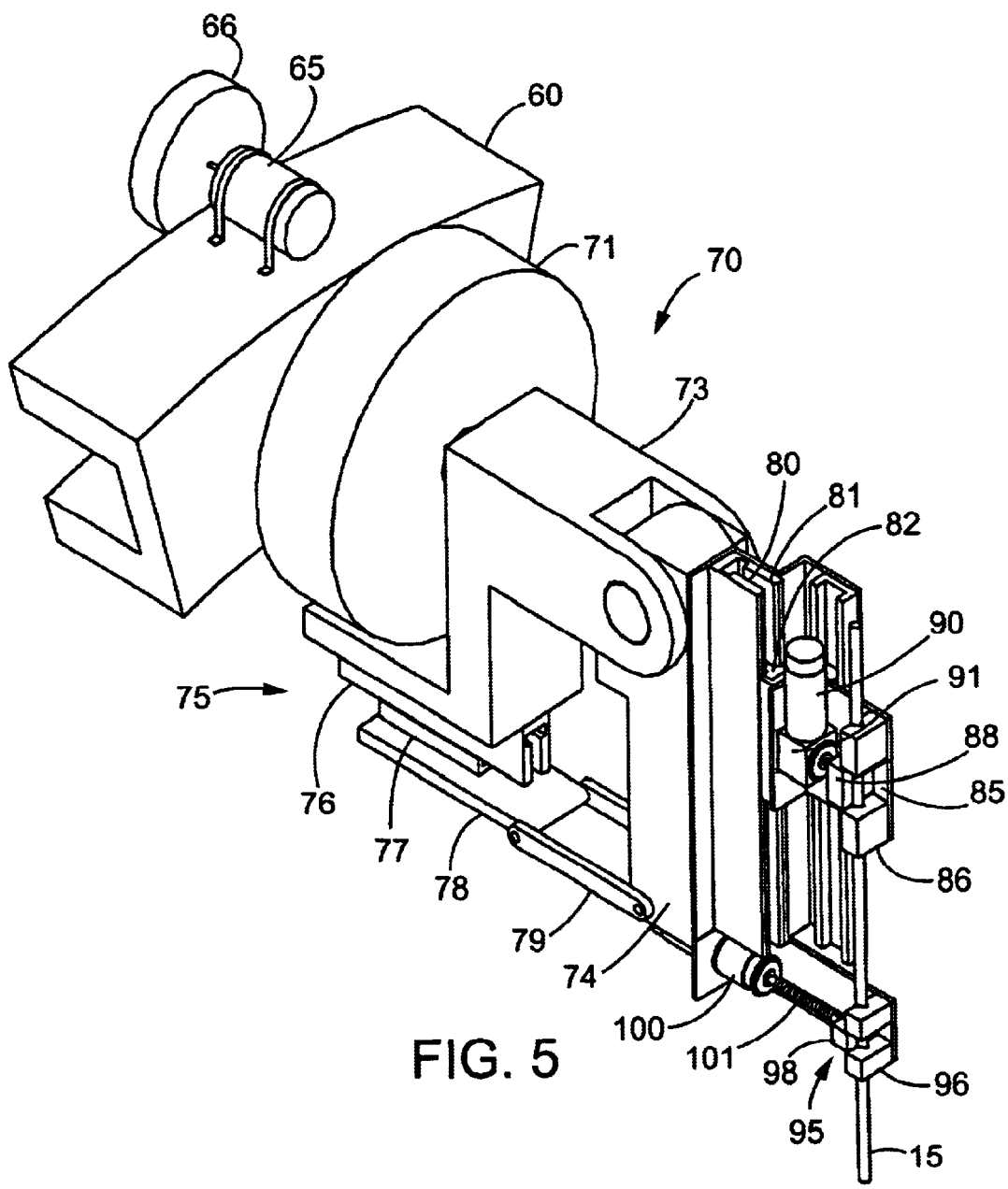
FIG. 5 is a schematic isometric of the carriage of the embodiment of FIG. 1.

Magnetic attraction can also be employed to hold a needle in the other embodiments of the present invention. For example, in the embodiment of FIG. 5, the fixed blocks 86, 96 of the clamps 85, 95 may be omitted and each of the movable blocks 88, 98 can be magnetized to hold the needle 15 by magnetic attraction.

In situations in which it is desired to determine the position of a needle in its lengthwise direction, instead of sensing the translation or rotation of an actuator which is translating the needle, it is possible to directly sense the lengthwise movement of the needle by various types of sensors. Biopsy needles are frequently manufactured with a plurality of parallel lines formed in their exterior surface at predetermined intervals by cutting, etching, chemical milling, or other methods. The lines will usually have a different (usually lower) reflectivity than the surface of the needle outside the lines. If a light source, such as an LED, is disposed so as to direct light at a needle formed with lines and a light-sensitive element, such as a photodiode, is disposed so as to receive light from the light source reflected off the needle, the intensity of the light incident upon the light-sensitive element will vary as the needle moves in its lengthwise direction and the light from the light source is reflected either off the lines or off other portions of the needle. For example, the reflected light may be of lesser intensity when reflected off one of the lines 16. An output signal from the light sensitive element will therefore have variations in amplitude, for example, or other characteristic corresponding to the variations in light intensity. By counting the variations in the output signal with a suitable signal processing circuit, it can be determined how many lines of the needle have passed through the light from the light source. Since the separation between adjacent lines is known in advance, the position of the needle in its lengthwise direction with respect to a reference position can be determined. A light source and a light-sensitive element can be disposed in any convenient location. For example, in the embodiment of FIG. 18, a light source 290 and a light-sensitive element 291 can be mounted on the second frame 260 supporting the needle 15. The light source 290 may be part of the manipulator, or it may be an external light source, such as sunlight or room lighting. Lines 16, other surface irregularities, or surface markings (such as painted stripes) producing a variation in the reflectivity of the surface of the needle 15 can be formed on the needle 15 with any desired spacing. The finer the spacing, the finer the resolution with which the position of the needle can be determined.

What is claimed is:

1. A manipulator for use in medical procedures comprising:
   a movable guide;
   a carriage mounted on and movable along the guide;
   an actuator operatively connected to the carriage for moving the carriage along the guide; and
   a positioning mechanism mounted on the carriage for holding a medical tool, the positioning mechanism including at least one actuator for moving the medical tool and being capable of moving the tool with at least two degrees of freedom with respect to the carriage including rotating the medical tool about a yaw axis and a pitch axis perpendicular to the yaw axis.

2. A manipulator as claimed in claim 1 wherein the guide includes an arch on which the carriage is movably mounted.

3. A manipulator as claimed in claim 2 wherein the arch has a shape of an arc of a circle.

4. A manipulator as claimed in claim 1 wherein the carriage is capable of rolling along the guide.

5. A manipulator as claimed in claim 1 wherein the positioning mechanism is capable of moving the tool in a lengthwise direction of the tool.

6. A manipulator as claimed in claim 5 wherein the positioning mechanism is capable of rotating the tool about a yaw axis perpendicular to the lengthwise direction of the tool.

7. A manipulator as claimed in claim 1 including a flexible member extending along the guide parallel to a path of movement of the carriage along the guide, wherein the actuator comprises a motor mounted on the carriage and a capstan rotated by the motor, the flexible member passing around the capstan.

8. A manipulator as claimed in claim 7 wherein the flexible member rests on the guide, and the capstan is spaced from the guide by approximately a thickness of the flexible member.

9. A manipulator as claimed in claim 7 wherein the motor is mounted on an interior of the carriage and extends into a recess in the guide.

10. A manipulator as claimed in claim 1 wherein the guide passes through a recess in the carriage.

11. A manipulator as claimed in claim 1 further including a table for supporting a patient and wherein the guide is movable in a lengthwise direction of the table.

12. A manipulator as claimed in claim 11 wherein the guide can roll along the table.

13. A manipulator as claimed in claim 11 wherein the guide is supported by the table.

14. An imaging arrangement comprising:
    a medical imaging device having a gantry and a table for supporting a patient extending into a bore of the gantry;
    a guide movable in a lengthwise direction of the table about a patient lying on the table;
    a carriage mounted on the guide for movement along the guide;
    a carriage actuator operatively connected to the carriage for moving the carriage along the guide;
    a medical tool mounted on the carriage, the guide being movable to a position in which the medical tool lies in a viewing field of the imaging device including the patient; and
    a positioning mechanism mounted on the carriage and including at least one actuator for moving the medical tool, the positioning mechanism being capable of moving the tool with respect to the carriage with at least three degrees of freedom including rotation of the tool about first and second axes perpendicular to a lengthwise direction of the tool and movement of the tool toward and away from a patient lying on the table.

15. An arrangement as claimed in claim 14 wherein the positioning mechanism can move the tool in a lengthwise direction of the tool.

16. An arrangement as claimed in claim 15 wherein the positioning mechanism can insert the tool into the patient lying on the table.

17. An arrangement as claimed in claim 14 wherein the guide can move in the lengthwise direction of the table into the bore of the gantry.

18. An arrangement as claimed in claim 14 wherein the guide is movably mounted on the table.

19. An arrangement as claimed in claim 14 wherein the guide has an arcuate portion, and the carriage is mounted on the arcuate portion.

20. An arrangement as claimed in claim 19 wherein the arcuate portion has a shape of an arc of a circle.

21. An arrangement as claimed in claim 14 including a distance sensor mounted on the positioning mechanism and an adjusting mechanism responsive to the distance sensor for automatically adjusting a distance of the tool from the patient lying on the table.

22. An arrangement as claimed in claim 21 wherein the adjusting mechanism comprises a parallel linkage mechanism.

23. An arrangement as claimed in claim 14 wherein the positioning mechanism includes a clamp capable of releasably grasping the tool, and an actuator for moving the clamp in a lengthwise direction of the tool into the patient.

24. An arrangement as claimed in claim 23 wherein the positioning mechanism includes a guide for guiding the tool as the tool is moved by the clamp.

25. An arrangement as claimed in claim 24 wherein the guide comprises a second clamp capable of releasably grasping the tool.

* * * * *